(12) United States Patent
Riley et al.

(10) Patent No.: US 7,504,088 B2
(45) Date of Patent: Mar. 17, 2009

(54) LIPOPHILIC DERIVATIVES OF CHELATE MONOAMIDES

(75) Inventors: Dennis Patrick Riley, Chesterfield, MO (US); William D. McGhee, Fenton, MO (US)

(73) Assignee: Kereos, Inc., St. Louis, MO (US)

( * ) Notice: Subject to any disclaimer, the term of this patent is extended or adjusted under 35 U.S.C. 154(b) by 576 days.

(21) Appl. No.: 11/146,651

(22) Filed: Jun. 7, 2005

(65) Prior Publication Data

US 2006/0008417 A1 Jan. 12, 2006

Related U.S. Application Data

(60) Provisional application No. 60/578,474, filed on Jun. 9, 2004, provisional application No. 60/605,180, filed on Aug. 27, 2004.

(51) Int. Cl.
*A61B 5/055* (2006.01)
(52) U.S. Cl. .................. 424/9.36; 424/9.3
(58) Field of Classification Search ............. 424/9.36, 424/9.363, 9.321; 514/124
See application file for complete search history.

(56) References Cited

U.S. PATENT DOCUMENTS

| | | | |
|---|---|---|---|
| 4,885,363 A | 12/1989 | Tweedle et al. |
| 4,927,623 A | 5/1990 | Long |
| 5,064,636 A | 11/1991 | Li et al. |
| 5,077,036 A | 12/1991 | Long |
| 5,114,703 A | 5/1992 | Wolf et al. |
| 5,120,527 A | 6/1992 | Li et al. |
| 5,155,215 A | 10/1992 | Ranney |
| 5,171,755 A | 12/1992 | Kaufman et al. |
| 5,304,325 A | 4/1994 | Kaufman et al. |
| 5,310,535 A | 5/1994 | Kruper et al. |
| 5,350,571 A | 9/1994 | Kaufman et al. |
| 5,358,704 A | 10/1994 | Desreux et al. |
| 5,393,524 A | 2/1995 | Quay |
| 5,403,575 A | 4/1995 | Kaufman et al. |
| 5,435,990 A | 7/1995 | Cheng et al. |
| 5,474,756 A | 12/1995 | Tweedle et al. |
| 5,512,294 A | 4/1996 | Li et al. |
| 5,542,935 A | 8/1996 | Unger et al. |
| 5,571,498 A | 11/1996 | Cacheris et al. |
| 5,573,752 A | 11/1996 | Ranganathan et al. |
| 5,614,170 A | 3/1997 | Cacheris et al. |
| 5,652,361 A | 7/1997 | Simon et al. |
| 5,674,470 A | 10/1997 | Tweedle et al. |
| 5,690,907 A | 11/1997 | Lanza et al. |
| 5,756,065 A | 5/1998 | Wilson et al. |
| 5,780,010 A | 7/1998 | Lanza et al. |
| 5,804,164 A | 9/1998 | Elgavish |
| 5,846,519 A | 12/1998 | Tweedle et al. |
| 5,909,520 A | 6/1999 | Garcia |
| 5,958,371 A | 9/1999 | Lanza et al. |
| 5,989,520 A | 11/1999 | Lanza et al. |
| 6,010,682 A | 1/2000 | Unger et al. |
| 6,056,939 A | 5/2000 | Desreux et al. |
| 6,132,764 A | 10/2000 | Li et al. |
| 6,143,274 A | 11/2000 | Tweedle et al. |
| 6,221,334 B1 | 4/2001 | Wedeking et al. |
| 6,676,929 B2 | 1/2004 | McMurry et al. |
| 2002/0127182 A1 | 9/2002 | Sherry et al. |
| 2004/0248856 A1* | 12/2004 | Lanza et al. ............. 514/124 |

FOREIGN PATENT DOCUMENTS

| | | |
|---|---|---|
| WO | WO-95/03829 | 2/1995 |
| WO | WO-99/58162 | 11/1999 |
| WO | WO-00/35488 | 6/2000 |
| WO | WO-00/35492 | 6/2000 |
| WO | WO-00/35887 | 6/2000 |
| WO | WO-02/060524 | 8/2002 |

OTHER PUBLICATIONS

Aime et al., Inorg. Chem. (1992) 31:2422-2428.
Bousquet et al., Radiology (1988) 166:693.
Caravan et al., Chem. Rev. (1999) 99:2293-2352.
Gali et al., Anticancer Res. (2001) 21:2785-2792.
Lanza et al., Circulation (1996) 94:3334-3340.
Margerstadt et al., Magn. Reson. Med. (1986) 3:808.
Runge et al., Radiology (1988) 166:835.
Sherry et al., Inorg. Chem. (1989) 28:620-622.
International Search Report for PCT/US05/19966, mailed on Oct. 26, 2005, 2 pages.

* cited by examiner

*Primary Examiner*—Michael G. Hartley
*Assistant Examiner*—James Rogers
(74) *Attorney, Agent, or Firm*—Morrison & Foerster LLP

(57) ABSTRACT

Compounds useful for associating with nanoparticle or microparticle emulsions to obtain magnetic resonance images permit control of the relaxivity of the signal and readily associate with the particulate components. The compounds are conveniently prepared from achiral derivatives of chelating moieties.

11 Claims, No Drawings

US 7,504,088 B2

LIPOPHILIC DERIVATIVES OF CHELATE MONOAMIDES

CROSS-REFERENCE TO RELATED APPLICATIONS

This application claims benefit of priority from U.S. provisional application Ser. Nos. 60/578,474 filed Jun. 9, 2004, and 60/605,180 filed Aug. 27, 2004, each of which is incorporated herein by reference.

TECHNICAL FIELD

The invention relates to diagnostic compositions, methods of their use, and methods for preparing the same.

BACKGROUND ART

The use of chelating agents of various types to entrap metal ions useful in magnetic resonance imaging is well known. Generally, the chelating agents contain a substantial number of unshared electron pairs or negatively charged or potentially negatively charged species. Perhaps the simplest among these is ethylenediaminetetraacetic acid (EDTA) commonly used as a water softener. Other chelating agents are diethylene triamine pentaacetic acid (DTPA), tetraazacyclododecanetetraacetic acid (DOTA), and their derivatives. In order to attach these chelating agents to additional moieties so as to permit other agents to be associated with them, the basic chelate nucleus has been derivatized. For example, U.S. Pat. No. 6,221,334 describes coupling folate receptor binding ligands to DOTA-type chelates.

One approach to such derivatization is exemplified in U.S. Pat. Nos. 5,652,361, 5,756,065, and 5,435,990, where the methylene group adjacent one of the carboxyl groups of DOTA is the point of attachment. This creates a chiral center, which enhances the complexity of any further reaction. In some cases, this methylene is coupled to a benzyl or phenyl moiety wherein the phenyl ring is substituted by a reactive group, such as isothiocyanate. The isothiocyanate provides a means for coupling to various additional compounds. As described in these patents, the isothiocyanate group can be used to couple the chelate to a targeting agent such as an antibody or fragment thereof.

Derivatized DOTA molecules are described for example, in U.S. Pat. Nos. 5,358,704; 4,885,363; 5,474,756; 5,674,470; 5,846,519; and 6,143,274, where the point of attachment is at one of the DOTA ring nitrogens. These derivatized DOTA molecules are stated, in these cases, to have the advantage of being neutral in solution. An additional patent that discloses attachment to the ring N of DOTA is U.S. Pat. No. 5,310,535. Other DOTA derivatives are described in U.S. Pat. No. 5,573,752, where one carboxyl is replaced with an amide, further bound to an aromatic system. Self-assembling forms of chelating agents are described in U.S. Pat. No. 6,056,939. (See also, Auffer, et al., *Chem. Rev.* (1999) 99:2293-2352; Gali, et al., *Anticancer Res.* (2001) 21:2785-2792; Sherry, et al., *Inorg. Chem.* (1989) 28:620-622; and Aime, et al., *Inorg. Chem.* (1992) 31:2422-2428).

There is an extensive literature on delivery vehicle compositions that have been used to administer chelated metals for MRI. Some of these compositions do not contain targeting agents, though others do comprise such agents. For example, U.S. Pat. Nos. 5,690,907; 5,780,010; 5,989,520; 5,958,371; and PCT publication WO 02/060524, the contents of which are incorporated herein by reference, describe emulsions of perfluorocarbon nanoparticles that are coupled to various targeting agents and to desired components, such as MRI imaging agents, radionuclides, and/or bioactive agents. Other compositions that have been used for targeted imaging include those disclosed in PCT publications WO 99/58162; WO 00/35488; WO 00/35887; and WO 00/35492, each of which is incorporated herein by reference.

Magnetic resonance imaging (MRI) has become a useful tool for diagnosis and for research. The current technology relies on detecting the energy emitted when the hydrogen nuclei in the water contained in tissues and body fluids returns to a ground state subsequent to excitation with a radio frequency. Observation of this phenomenon depends on imposing a magnetic field across the area to be observed, so that the distribution of hydrogen nuclear spins is statistically oriented in alignment with the magnetic field, and then imposing an appropriate radio frequency. This results in an excited state in which this statistical alignment is disrupted. The decay of the distribution to the ground state can then be measured as an emission of energy, the pattern of which can be detected as an image.

However, the relaxation rate of the relevant hydrogen nuclei in the above described process is too slow to generate detectable amounts of energy, as a practical matter. To create a detectable signal, the area to be imaged is supplied with a contrast agent, generally a strongly paramagnetic metal, which effectively acts as a catalyst to accelerate the decay, thus permitting sufficient energy. Thus, contrast agents decrease the relaxation time and increase the reciprocal of the relaxation time—i.e., the "relaxivity" of the surrounding hydrogen nuclei.

Two types of relaxation times can be measured. $T_1$ is the time for the magnetic distribution to return to 63% of its original distribution longitudinally with respect to the magnetic field and the relaxivity $\tau_1$, is its reciprocal. $T_2$ measures the time wherein 63% of the distribution returns to the ground state transverse to the magnetic field. Its reciprocal is the relaxivity index $\tau_2$. In general, the relaxation times and relaxivities will vary with the strength of the magnetic field; this is most pronounced in the case of the longitudinal component.

Contrast agents which are based on chelated paramagnetic metal have been described. For example, U.S. Pat. Nos. 5,512,294 and 6,132,764 describe liposomal particles with metal chelates on their surfaces as MRI contrast agents. U.S. Pat. Nos. 5,064,636 and 5,120,527 describe paramagnetic oil emulsions for MRI in the gastrointestinal tract. U.S. Pat. Nos. 5,614,170 and 5,571,498 describe emulsions that incorporate lipophilic gadolinium chelates, e.g., gadolinium diethylenetriaminepentaacetic acid-bisoleate (Gd-DTPA-BOA) as blood pool contrast agents. U.S. Pat. No. 5,804,164 describes water-soluble, lipophilic agents which comprise particularly designed chelating agents and paramagnetic metals. U.S. Pat. No. 6,010,682 and other members of the same patent family describe lipid soluble chelating contrast agents containing paramagnetic metals which are said to be able to be administered in the form of liposomes, micelles or lipid emulsions. Thus, in general, contrast agents may take the form of paramagnetic metals such as rare earth metals or iron mobilized in a form that permits substantial concentrations of the paramagnetic metal to be delivered to the desired imaging area.

DISCLOSURE OF THE INVENTION

The present invention provides diagnostic compositions, methods of their use, and methods of preparing the same.

In one aspect, the present invention provides chelating agents useful for supporting metal ions employed, for example, in magnetic resonance imaging (MRI) where the chelate is supplied in a carrier which comprises lipophilic particles or droplets. More specifically, the invention is directed to chelating agents coupled through their monoamide derivatives to phosphoglycerides. The present invention also provides contrast agents having an enhanced relaxivity for both $\rho_1$ and $\rho_2$.

The invention also provides compounds which can readily be associated with carriers of a variety of lipophilic delivery vehicles such as liposomes, fluorocarbon nanoparticles, oil droplets, and the like in a position relative to these delivery vehicles that provides for control of relaxivity of the signal and also provides, if desired, a mechanism for facilitating excretion of the potentially toxic paramagnetic ion that enhances the resonance image.

It is also advantageous to facilitate the excretion of the paramagnetic ion, which may otherwise be toxic if it is retained in a subject. Thus, it would be advantageous to provide a site for cleaving the chelated metal ion from the particles or from any lipid components that might result in cellular or liver uptake. As an alternative to chelation of a paramagnetic ion, a radioactive nuclide may be included; the desirability of facilitating excretion of this nuclide is also apparent.

In one embodiment, the present invention provides a compound having the formula (1), which may contain a paramagnetic or radionuclide in the chelating moiety:

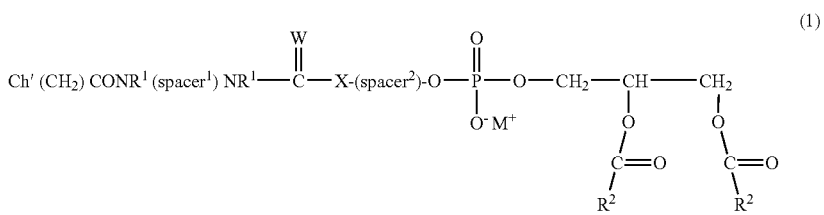

(1)

wherein Ch' is a residue of a chelating agent comprising at least four nitrogen atoms and (n−1) carboxyl groups, where n is the number of nitrogen atoms in the chelating moiety;
W is O or S;
X is $NR^1$, S or O;
M+ is a counter-ion;
each $R^1$ is H or alkyl (1-4C);
each $R^2$ is an optionally substituted saturated or unsaturated hydrocarbyl group containing at least 10C;
spacer$^1$ comprises a $C_{1-10}$ alkyl optionally containing a heteroatom, aryl, a peptide or a polyalkylene glycol;
spacer$^2$ comprises a $C_{1-10}$ alkyl optionally containing a heteroatom;
and wherein said compound is negatively charged when dissolved in water under physiological conditions.

In another embodiment, the present invention provides compounds of formula (1A)

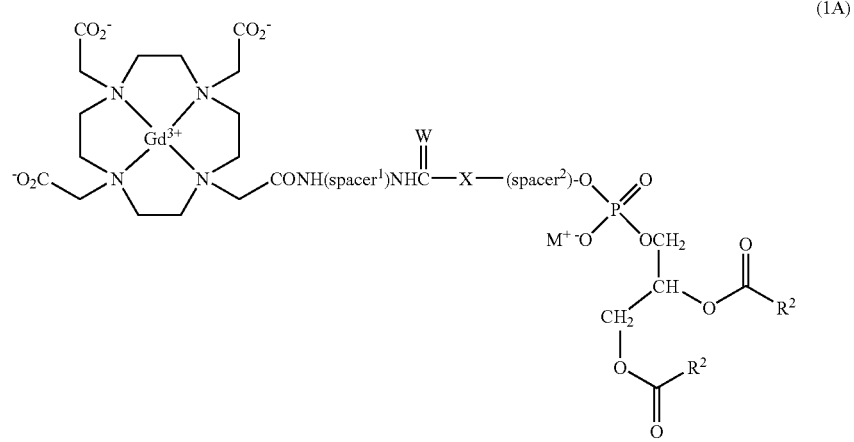

(1A)

where W, X, spacer¹, spaces and R² are defined in formula 1.

In yet another embodiment, the present invention provides compounds having formula (1B)

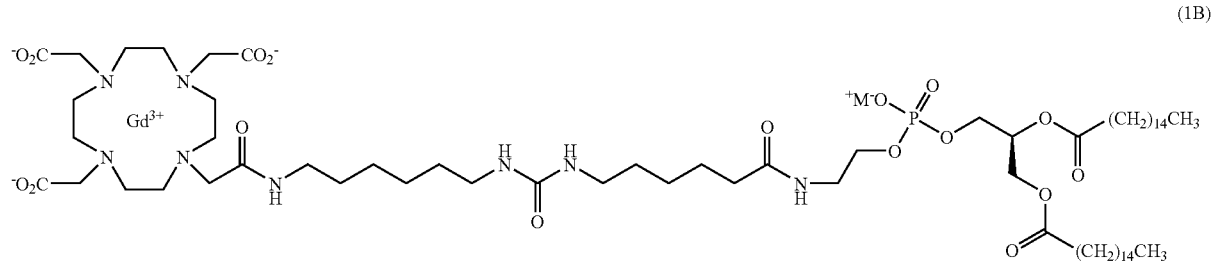

(1B)

In each of the above formula, Ch' may be derived from a DOTA residue, having one less carboxyl group which is derivatized as an amide. In one example, Ch' comprises a Gd(3+) chelate. In particular examples, Ch' may be a Gd(3+) chelate of a DOTA residue, such as those derived from 1,4,7,10-tetraazacyclodecane-1,4,7-triacetic acid.

In each of the above formula, each $R^1$ may be H.

In each of the above formula, the spacer¹ and spaces may comprise substituents which are sufficiently inert to preclude interference with reaction of the diamine comprising spacer¹ with the carboxyl group of the chelating moiety, and the reaction of the resulting amine with an amino group coupled to spacer² in the presence of phosgene or phosgene equivalent, or a carbonyl inserting reagent such as $CO_2$.

In each of the above formula, spacer¹ may be ethylene, tetramethylene, hexamethylene, or phenylene. In one example, spacer¹ isp-phenylene. In another example, spacer¹ is hexamethylene.

In each of the above formula, spacer² may be ethylene, or

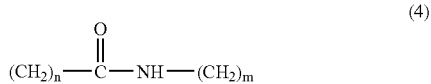

(4)

wherein n is 1-6 and m is 1-6.

In each of the above formula, $M^+$ is a counter-ion, including but not limited to alkali and alkaline earth metal ions, as well as inorganic salts such as ammonium, and other counter-ions known in the art. Suitable counterions include, but are not limited to, $Na^+$, $K^+$, $½Ca^{2+}$, $R_3NH^+$, $R^4N^+$, and $NR_4^+$, wherein each $R_4$ is an H or alkyl.

In each of the above formula, $R^2COO$ may be a residue of a naturally occurring fatty acid or a mixture of said residues.

The compounds of the present invention are conveniently prepared by a small number of reactions which avoid the complications introduced by having new additional chiral centers, for example, by avoiding the separation of diastereomers in the final product. In particular, the chelator moiety is achiral, which when conjugated to a chiral phospholipid results in an asymmetric compound having no additional chiral centers.

The compounds of the present invention may also comprise a paramagnetic metal ion or a radionuclide, which is chelated to the chelating moiety (Ch'). In one embodiment, the paramagnetic metal ion is nonradioactive.

In additional aspects, the invention is directed to compositions comprising lipophilic delivery vehicles associated with compounds having any one of the above formula, and methods to obtain magnetic resonance or radionuclide images using these compositions. For example, the compounds of any of the above formula may be covalently or non-covalently associated with a liphophilic nanoparticle or microparticle. In a particular example, the nanoparticle or microparticle comprises at least 2,000 copies of the compound.

In one embodiment, the present invention provides compositions comprising a compound having any one of the above formula, and a lipophilic nanoparticle or microparticle, wherein the nanoparticle or the microparticle optionally comprises a targeting agent and/or a biologically active agent. The targeting agent may be a receptor ligand or an antibody or fragment thereof. The nanoparticle or microparticle may be a liposome, an oil droplet, a perfluorocarbon nanoparticle, a lipid-coated protein particle, or a lipid-coated polysaccharide.

In another aspect, the invention is directed to methods for preparing compounds having any one of the above formula, and to methods for preparing the delivery vehicle compositions of the invention.

In one embodiment, the present invention provides a method to prepare the compound of the formula (1)

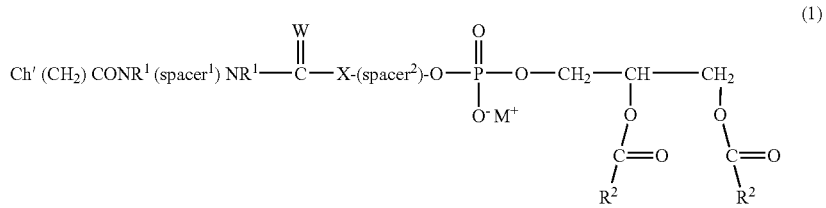

(1)

comprising contacting a compound of the formula

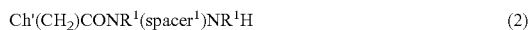

Ch'(CH$_2$)CONR$^1$(spacer$^1$)NR$^1$H    (2)

with CO$_2$, phosgene, or phosgene equivalent, or with CS$_2$, thiophosgene, or thiophosgene equivalent and a compound of the formula:

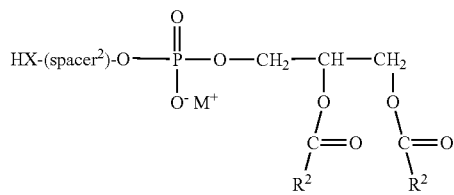

(3)

wherein Ch', X, R$^1$, R$^2$, spacer$^1$ and spacer$^2$ are as defined in claim 1.

In one example, the phosgene equivalent is triphosgene, diphosgene, carbonyl diimidazole, or p-nitrophenyl chloroformate.

In another example, the Ch' in formula (2) is a residue of 1,4,7,10-tetra-azacyclododecane-N,N',N'',N'''-tetraacetic acid (DOTA) having one less carboxyl group than DOTA. The Ch' may further comprise a paramagnetic ion, particularly a nonradioactive paramagnetic ion. For example, the paramagnetic ion may be Gd(3+).

The yet another example, the methods of preparing formula (1) as described above further comprises contacting the compound having formula (1) with a paramagnetic ion, particularly a nonradioactive paramagnetic ion. For example, a compound having formula (1) wherein Ch' is a residue of 1,4,7,10-tetra-azacyclododecane-N,N',N'',N'''-tetraacetic acid (DOTA) having one less carboxyl group than DOTA, may be contacted with GdCl$_3$ or Gd$_2$O$_3$.

The present invention also provides methods of obtaining magnetic resonance imaging using the compounds and compositions of the present invention. In one embodiment, the present invention provides a method for imaging a sample, comprising contacting the sample with a compound having any one of the above formula, and imaging said sample. The present invention also provides a method for imaging a sample, comprising contacting the sample with a composition comprising a compound having any one of the above formula, and a lipophilic nanoparticle or a microparticle optionally comprising a targeting agent and/or a biologically active agent, and imaging said sample. In one embodiment, the sample is a tissue sample.

These compounds of the present invention are negatively charged by virtue of the appended phosphodiester. In other circumstances, other linkers that contain negatively charged groups which add to the overall net negative charge of the molecules may be advantageous. For example, in certain emulsion formulations, negatively charged groups that add to the overall net negative charge of the molecule may keep the chelating molecule in the water phase.

One method for providing useful concentrations of contrast agents has been described in U.S. Pat. Nos. 5,780,010 and 5,909,520. A nanoparticle is formed from an inert core surrounded by a lipid/surfactant coating. The chelating agent containing a paramagnetic metal ion and the targeting ligand can be modified so that they are attached to a lipophilic tail, which may associate with the lipid/surfactant coating surrounding the fluorocarbon nanoparticle. Copending application U.S. Ser. No. 10/765,299 filed 26 Jan. 2004, incorporated herein by reference, also describes a method for providing chelating agents with a lipophilic moiety that distances the chelate from the surface of the particulate layer.

The present invention is an alternative method from copending application U.S. Ser. No. 10/765,299 for providing chelating agents with a lipophilic moiety that distances the chelate from the surface of the particulate layer. The present invention in one embodiment is focused on improvements in the contrast agents useful in magnetic resonance imaging. In one aspect, the present invention provides an improvement in the design of contrast agents whereby the relaxivity of the signal can be controlled, and excretion can be facilitated. The compounds of the invention, however, are useful in other contexts as well, such as delivering radionuclides to desired locations for imaging based on nuclear emissions.

Modes of Carrying Out the Invention

In general, the invention is directed to compounds of formula (I), (1A), and (1B) including these compounds which comprise a paramagnetic metal ion or a radionuclide.

The compounds as described herein, when they include an appropriate paramagnetic ion, provide a conveniently prepared MRI contrast agent that has at least two useful features. First, by virtue of its coupling to a phospholipid, it is readily associated with lipophilic delivery vehicles such as liposomes, fluorocarbon nanoparticles, and the like. Second, because it may contain a spacer, the relaxivity of the signal can be controlled by the distance imposed by the spacer from the supporting delivery vehicles. An optional third advantage is that the spacer may provide a cleavage site which permits the contrast agent to be dissociated from the particles and excreted once the image is obtained. Alternatively, the cleavage site utilized may be that of the amide formed between the carboxyl group of the chelating agent and the diamine.

The compounds of the present invention are conveniently prepared by reaction of a diamine with the chelating agent, such as DOTA, controlling the number of carboxyl groups reacted through dilution and stoichiometry. This is followed by reaction of the resulting intermediate amide with phosphatidylethanolamine or an analog thereof containing a different (other than CH$_2$CH$_2$) spacer (spacer$^2$), between the phosphate and the amino group. Thus, although less convenient, phosphatidyl methanolamine or phosphatidyl propanolamine would result in a satisfactory product. Spacer$^1$ and spacer$^2$ are selected such that they contain at least one methylene group, but may contain additional linking atoms or substituents so long as these do not interfere with the synthesis steps. Thus, for example, diamines containing ether linkages may be employed in the synthesis as the spacer$^1$-diamine. Coupling can be performed to a wide variety of spacers and phospholipids.

The chelating agent may be any chelating moiety having one less carboxyl group than its underivatized form. In particular examples, the chelating agent comprises at least four, or a multiplicity of nitrogens spaced by alkylene groups and to which carboxylic acid-bearing moieties are coupled, less the derivatized carboxyl group depicted in formula 1. Chelating agents are characterized by comprising a multiplicity of unshared electron pairs or potential negative charges which serve to sequester the desired metal ion. Commonly employed chelating agents include porphyrins; ethylenediaminetetraacetic acid (EDTA); diethylenetriamine-N,N,N', N'',N''-pentaacetate (DTPA); 1,4,10,13-tetraoxa-7,16-diazacyclo-octadecane-7 (ODDA); 16-diacetate-N-2-(azol-1 (2)-yl)ethyliminodiacetic acids; 1,4,7,10-tetra-azacyclododecane-N,N',N'',N'''-tetraacetic acid (DOTA); 1,7,13-triaza-4,10,16-trioxacyclooctadecane-N,N',N''-triacetate (TTTA); tetraethylene glycols; 1,5,9-triazacyclododecane-N,N',N'',-tris(methylenephosphonic acid (DOTRP);

N,N',N"-trimethylammonium chloride (DOTMA) and analogues thereof. A particular chelating agent in the compounds of the invention is DOTA.

The purpose of the chelating agent is to sequester the desired paramagnetic metals or radionuclides. Illustrative paramagnetic metals include but are not limited to a lanthanide element of atomic numbers 58-70 or a transition metal of atomic numbers 21-29, 42 or 44, i.e., for example, scandium, titanium, vanadium, chromium, manganese, iron, cobalt, nickel, copper, molybdenum, ruthenium, cerium, praseodymium, neodymium, promethium, samarium, europium, gadolinium, terbium, dysprosium, holmium, erbium, thulium, and ytterbium, particularly Gd(III), Mn(II), iron, europium and/or dysprosium. Suitable radionuclides include the radioactive forms of, for example, Sm, Ho, Y, Pm, Gd, La, Lu, Yb, Sc, Pr, Tc, Re, Ru, Rh, Pd, Pt, Cu, Au, Ga, In, Sn, and Pb. The present invention also encompasses compositions comprising other exemplary radionuclides and paramagnetic ions known in the art.

The phosphoglyceride included in each of the above formula may be derived from naturally occurring lecithins, wherein the groups represented by $R^2COO$ are fatty acids, such as oleic, palmitic, stearic; and the like. However, equally useful in the method of the invention are phosphoglycerides where each $R^2$ is an optionally substituted hydrocarbyl moiety which may be saturated or unsaturated. The hydrocarbyl moiety may contain at least 10C in order to confer sufficient lipophilicity; however, the carbons may be spaced apart by one or two heteroatoms selected from O, N or S. Suitable substituents include substituents that comprise aromatic moieties including heteroatom-containing aromatic moieties, and/or the substituents may be halo, =O, OR, SR, and $NR_2$ wherein each R is independently an optionally substituted alkyl (1-6C). The hydrocarbyl moiety represented by $R^2$ may be branched or straight chain and may comprise one or more cyclic portions.

In one embodiment, $R^2$ is an optionally substituted saturated or unsaturated hydrocarbyl group containing at least 10C. In other embodiments, $R^2$ may have less than 10 carbons. In general, each $R^2$ is simply of sufficient lipophilicity to provide a means for association with the lipophilic particulates or droplets that comprise the carrier. The skilled artisan can readily select embodiments for $R^2$ which fulfill this condition.

The $spacer^1$ may include portions derived from peptides, pseudopeptides, polyalkylene glycols, such as polyethylene glycol, and the like. (Pseudopeptides are polymers similar to peptides where the peptide linkages have been replaced by isosteric linkages—i.e., wherein CONH linkages are replaced, for example, with $CH_2NH$, CH=CH, and the like.) The length of the spacer may be chosen to control the relaxivity of the signal as described hereinbelow, and further may contain a cleavage site which permits release of the chelate from the carrier particle. Particular embodiments of $spacer^1$ include ethylene, tetramethylene, hexamethylene, or p-phenylene.

The $spacer^2$ may include a portion which has its origin in the phosphatidylglyceride itself—for example, in one embodiment, the spacer may be or include the moiety $CH_2CH_2$ included in a phosphatidyl ethanolamine, wherein the $NR^1$ shown adjacent to $spacer^2$ is derived from a phosphatidyl ethanolamine.

In one embodiment, $spacer^2$ is ethylene or

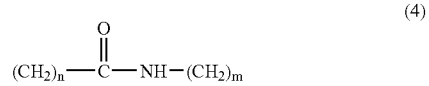

wherein n is 1-6 and m is 1-6.

In other embodiments, m and n in formula (4) may be greater than 6.

Particular embodiments of $R^1$ include methyl, ethyl and H. In one embodiment, each $R^1$ is H.

In general, the compounds of formula (1) and (1A) are synthesized from a compound of the formula:

with $CO_2$, phosgene or phosgene equivalent, or with $CS_2$, thiophosgene or a thiophosgene equivalent and a compound of the formula:

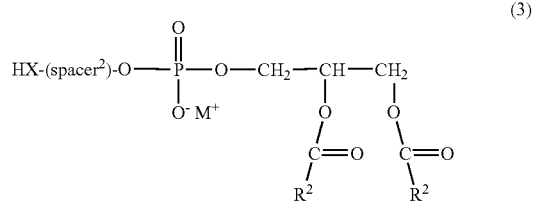

wherein Ch', X, $spacer^1$, $spacer^2$, $R^1$ and $R^2$ are defined as above.

Each $spacer^1$ and $spacer^2$ may further contain substituents that do not interfere with the reaction described above.

Examples of phosgene equivalents include but are not limited to triphosgene, diphosgene, carbonyl diimidazole, p-nitrophenyl chloroformate, and others known to those skilled in the art. Examples of thiophosgene equivalents include but are not limited to thiocarbonyl diimidazole and others known to those skilled in the art.

One way of preparing the compound of formula (2) comprises contacting a compound of the formula

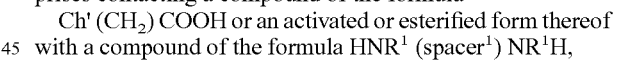

with a compound of the formula $HNR^1$ ($spacer^1$) $NR^1H$, wherein $R^1$ and Ch' are defined as above. For this reaction, the composition of spacer, is such that it does not interfere with this reaction or the subsequent reaction to form the final product of formula (1).

In one embodiment, compounds of formula (2) may be prepared by i) reacting a precursor Ch' compound underivatized with carboxyl groups with a compound of the formula $Y(CH_2)CONR^1(spacer^1)NR^1(P)$ to provide an intermediate; ii) reacting the intermediate with $YCH_2CO_2A$; and iii) deprotecting the protected group;

where Ch' and $R^1$ are as defined above;

each Y is a suitable leaving group;

P is a suitable nitrogen protecting group; and

A is a suitable alkyl or aralkyl group.

Examples of suitable leaving groups include but are not limited to Cl, Br, I, OTosyl, and the like.

Examples of suitable nitrogen protecting groups include but are not limited to Boc, cbz, fmoc, etc.

Examples of suitable $R^2$ groups include but are not limited to $CH_3$, $CH_3CH_2$, $CH_2Ph$ etc.

The compounds as described herein may be bound to a metal, and may be included in compositions which contain lipophilic delivery vehicles. "Delivery vehicles" are particulate carriers that are, at least on their surface, lipophilic and which are suspended in a hydrophilic or aqueous medium. These vehicles are microparticles or nanoparticles, and may have average diameters in the range of 10 nm-100 WAM, preferably 50 nm-50 µm. However, for in vivo use, particles having diameters in the range of 50-500 nm, or preferably 50-300 nm. The particles may be of a variety of compositions, including such well known vehicles as liposomes, which may be of various sizes and may be unilamellar or multilamellar, micelles, oil droplets, lipoproteins, such as HDL, LDL, IDL (intermediate density lipoproteins), VLDL (very low density lipoproteins), chylomicrons, fluorocarbon nanoparticles, microbubbles or nanobubbles, or any of a wide variety of particles in the above mentioned size range that are lipophilic at least at their surface, as further described below. Thus, the surface of these nanoparticles will comprise lipids or surfactants or both.

The compounds as described herein, when associated with a paramagnetic ion and the lipophilic particles contained in a carrier system are useful in obtaining magnetic resonance images. The vehicles in the delivery system may further comprise other useful components such as targeting agents to carry the contrast agent to the desired tissue or organ and may optionally contain therapeutic or other biologically active agents. In some embodiments, these vehicles may also comprise other imaging agents such as radionuclides, or, more commonly, include the radionuclides, in the alternative, in the chelate.

Targeting agents typically may comprise antibodies or immunospecific fragments thereof, ligands for receptors present on the desired target or tissue, molecules designed specifically to target cellular components such as those designed based on cyclic RGD peptides designed to target integrins and the like. The lipophilic particles themselves may include reactive groups that can be coupled to targeting agents.

Lipid/surfactant components of the delivery vehicles can be coupled to these reactive groups through functionalities contained in the lipid/surfactant component. For example, phosphatidylethanolamine may be coupled through its amino group directly to a desired moiety, or may be coupled to a linker such as a short peptide which may provide carboxyl, amino, or sulfhydryl groups as described below. Alternatively, standard linking agents such a maleimides may be used. A variety of methods may be used to associate the targeting ligand and the ancillary substances to the nanoparticles; these strategies may include the use of spacer groups such as polyethylene glycol or peptides, for example.

For coupling by covalently binding the targeting ligand or other organic moiety to the components of the outer layer, various types of bonds and linking agents may be employed. Typical methods for forming such coupling include formation of amides with the use of carbodiamides, or formation of sulfide linkages through the use of unsaturated components such as maleimide. Other coupling agents include, for example, glutaraldehyde, propanedial or butanedial, 2-iminothiolane hydrochloride, bifunctional N-hydroxysuccinimide esters such as disuccinimidyl suberate, disuccinimidyl tartrate, bis[2-(succinimidooxycarbonyloxy)ethyl]sulfone, heterobifunctional reagents such as N-(5-azido-2-nitrobenzoyloxy)succinimide, succinimidyl 4-(N-maleimidomethyl)cyclohexane-1-carboxylate, and succinimidyl 4-(p-maleimidophenyl)butyrate, homobifunctional reagents such as 1,5-difluoro-2,4-dinitrobenzene, 4,4'-difluoro-3,3'-dinitrodiphenylsulfone, 4,4'-diisothiocyano-2,2'-disulfonic acid stilbene, p-phenylenediisothiocyanate, carbonylbis(L-methionine p-nitrophenyl ester), 4,4'-dithiobisphenylazide, erythritolbiscarbonate and bifunctional imidoesters such as dimethyl adipimidate hydrochloride, dimethyl suberimidate, dimethyl 3,3'-dithiobispropionimidate hydrochloride and the like. Linkage can also be accomplished by acylation, sulfonation, reductive amination, and the like. A multiplicity of ways to couple, covalently, a desired ligand to one or more components of the outer layer is well known in the art. The ligand itself may be included in the surfactant layer if its properties are suitable. For example, if the ligand contains a highly lipophilic portion, it may itself be embedded in the lipid/surfactant coating. Further, if the ligand is capable of direct adsorption to the coating, this too will effect its coupling. For example, nucleic acids, because of their negative charge, adsorb directly to cationic surfactants.

The targeting ligand or antibody may bind directly to the nanoparticle, i.e., the ligand or antibody is associated with the nanoparticle itself, as described above. Alternatively, indirect binding such as that effected through biotin/avidin may be employed. Typically, in biotin/avidin mediated targeting, the ligand or antibody is coupled not to the emulsion, but rather coupled, in biotinylated form, to the targeted tissue.

Ancillary agents that may be coupled to the nanoparticles through entrapment in the coating layer include radionuclides, instead of, or in addition to, the paramagnetic ion. Radionuclides may be either therapeutic or diagnostic; diagnostic imaging using such nuclides is well known and by targeting radionuclides to undesired tissue a therapeutic benefit may be realized as well. Typical diagnostic radionuclides include $^{99m}Tc$, $^{95}Tc$, $^{111}In$, $^{62}Cu$, $^{64}Cu$, $^{67}Ga$, and $^{68}Ga$, and therapeutic nuclides include 186Re, $^{188}Re$, $^{153}Sm$, $^{166}Ho$, $^{177}Lu$, $^{149}Pm$, 90Y, $^{212}Bi$, $^{103}Pd$, $^{109}Pd$ $^{159}Gd$, $^{140}La$, $^{198}Au$, $^{199}Au$, 169Yb, $^{175}Yb$, $^{165}Dy$ $^{166}Dy$, $^{67}Cu$, $^{105}Rh$, $^{111}Ag$, and $^{192}Ir$. The nuclide can be provided to a preformed emulsion in a variety of ways. For example, $^{99}Tc$-pertechnate may be mixed with an excess of stannous chloride and incorporated into the preformed emulsion of nanoparticles. Stannous oxinate can be substituted for stannous chloride. In addition, commercially available kits, such as the HM-PAO (exametazine) kit marketed as Ceretekg by Nycomed Amersham can be used. Means to attach various radioligands to the nanoparticles of the invention are understood in the art. As stated above, the radionuclide may not be an ancillary material, but may instead occupy the chelating agent in lieu of the paramagnetic ion when the composition is to be used solely for diagnostic or therapeutic purposes based on the radionuclide.

Other ancillary agents include fluorophores such as fluorescein, dansyl, and the like.

Included in the lipophilic carrier vehicle as ancillary agents, in some embodiments of the invention, are biologically active agents. These biologically active agents can be of a wide variety, including proteins, nucleic acids, pharmaceuticals, and the like. Thus, included among suitable pharmaceuticals are antineoplastic agents, hormones, analgesics, anesthetics, neuromuscular blockers, antimicrobials or antiparasitic agents, antiviral agents, interferons, antidiabetics, antihistamines, antitussives, anticoagulants, and the like.

In all of the foregoing cases, whether the associated moiety is a targeting ligand for a tissue or organ or is an ancillary agent, the defined moiety may be non-covalently associated with the lipophilic vehicle, may be directly coupled to the components of the vehicle, or may be coupled to said components through spacer moieties.

A multiplicity of vehicles may be used in the compositions of the invention, for example, liposomal particles. The literature describing various types of liposomes is vast and well known to practitioners. As the liposomes themselves are comprised of lipid moieties, the above-described lipids and surfactants are applicable in the description of moieties contained in the liposomes themselves. These lipophilic components can be used to couple to the chelating agent in a manner similar to that described above with respect to the coating on the nanoparticles having an inert core. Micelles are composed of similar materials, and this approach to coupling desired materials, and in particular, the chelating agents applies to them as well. Solid forms of lipids may also be used.

In another example, proteins or other polymers can be used to form the particulate carrier. These materials can form an inert core to which a lipophilic coating is applied, or the chelating agent can be coupled directly to the polymeric material through techniques employed, for example, in binding affinity reagents to particulate solid supports. Thus, for example, particles formed from proteins can be coupled to tether molecules containing carboxylic acid and/or amino groups through dehydration reactions mediated, for example, by carbodiimides. Sulfur-containing proteins can be coupled through maleimide linkages to other organic molecules which contain tethers to which the chelating agent is bound. Depending on the nature of the particulate carrier, the method of coupling so that an offset is obtained between the dentate portion of the chelating agent and the surface of the particle will be apparent to the ordinarily skilled practitioner.

In still another example, PCT publication WO95/03829 describes oil emulsions where the drug is dispersed or solubilized inside an oil droplet and the oil droplet is targeted to a specific location by means of a ligand. U.S. Pat. No. 5,542,935 describes site-specific drug delivery using gas-filled perfluorocarbon microspheres. The drug delivery is accomplished by permitting the microspheres to home to the target and then effecting their rupture. Low boiling perfluoro compounds are used to form the particles so that the gas bubbles can form.

One embodiment comprises emulsions wherein the nanoparticles are based on high boiling perfluorocarbon liquids such as those described in U.S. Pat. No. 5,958,371 referenced above. The liquid emulsion contains nanoparticles comprised of relatively high boiling perfluorocarbons surrounded by a coating which is composed of a lipid and/or surfactant. The surrounding coating is able to couple directly to a targeting moiety or can entrap an intermediate component which is covalently coupled to the targeting moiety, optionally through a linker, or may contain a non-specific coupling agent such as biotin. Alternatively, the coating may be cationic so that negatively charged targeting agents such as nucleic acids, in general or aptamers, in particular, can be adsorbed to the surface.

One useful emulsion is a nanoparticulate system containing a high boiling perfluorocarbon as a core and an outer coating that is a lipid/surfactant mixture which provides a vehicle for binding a multiplicity of copies of one or more desired components to the nanoparticle. The construction of the basic particles and the formation of emulsions containing them, regardless of the components bound to the outer surface is described in the above-cited patents, and in U.S. Pat. Nos. 5,690,907, 5,780,010, 5,989,520 and 5,958,371, each incorporated herein by reference.

The high boiling fluorochemical liquid is such that the boiling point is higher than that of body temperature—i.e., 37° C. Thus, fluorochemical liquids which have boiling points at least 30° C. are preferred, more preferably 37° C., more preferably above 50° C., and most preferably above about 90° C. The "fluorochemical liquids" useful in the invention include straight and branched chain and cyclic perfluorocarbons including perfluorinated compounds which have other functional groups. "Perfluorinated compounds" includes compounds that are not pure perfluorocarbons but rather wherein other halo groups may be present. These include perfluorooctylbromide, and perfluorodichlorooctane, for example.

Useful perfluorocarbon emulsions are disclosed in U.S. Pat. Nos. 4,927,623, 5,077,036, 5,114,703, 5,171,755, 5,304,325, 5,350,571, 5,393,524, and 5,403,575, which are incorporated herein by reference, and include those in which the perfluorocarbon compound is perfluorodecalin, perfluorooctane, perfluorodichlorooctane, perfluoro-n-octyl bromide, perfluoroheptane, perfluorodecane, perfluorocyclohexane, perfluoromorphol ine, perfluorotripropylamine, perfluortributylamine, perfluorodimethylcyclohexane, perfluorotrimethylcyclohexane, perfluorodicyclohexyl ether, perfluoro-n-butyltetrahydrofuran, and compounds that are structurally similar to these compounds and are partially or fully halogenated (including at least some fluorine substituents) or partially or fully fluorinated including perfluoroalkylated ether, polyether or crown ether.

It will be noted, that in addition to high boiling halo carbons, the particles useful in the compositions of the invention may contain microbubbles or nanobubbles. Thus, lower boiling components of the particles may be employed such that at temperatures in vivo effect vaporization.

In addition, lipoproteins and chylomicrons may also be used. Various types of lipoprotein are well known and include, for example, LDL, HDL, and VLDL.

In one embodiment, lipid/surfactant coated nanoparticles may be formed by microfluidizing a mixture of a fluorocarbon lipid which forms the core and a lipid/surfactant mixture which forms the outer layer in suspension in aqueous medium to form an emulsion. In this procedure, the lipid/surfactants may already be coupled to additional ligands when they are coated onto the nanoparticles, or may simply contain reactive groups for subsequent coupling. Alternatively, the components to be included in the lipid/surfactant layer may simply be solubilized in the layer by virtue of the solubility characteristics of the ancillary material. Sonication or other techniques may be required to obtain a suspension of the lipid/surfactant in the aqueous medium. Typically, at least one of the materials in the lipid/surfactant outer layer comprises a linker or functional group which is useful to bind an additional desired component or the component may already be coupled to the material at the time the emulsion is prepared.

The lipid/surfactants used to form an outer coating on the delivery vehicles (that will contain the coupled ligand or entrap reagents for binding desired components to the surface) include natural or synthetic phospholipids, fatty acids, cholesterols, lysolipids, sphingomyelins, and the like, including lipid conjugated polyethylene glycol. Various commercial anionic, cationic, and nonionic surfactants can also be employed, including Tweens, Spans, Tritons, and the like. Some surfactants are themselves fluorinated, such as perfluorinated alkanoic acids such as perfluorohexanoic and perfluorooctanoic acids, perfluorinated alkyl sulfonamide, alkylene quaternary ammonium salts and the like. In addition, perfluorinated alcohol phosphate esters can be employed. Cationic lipids included in the outer layer may be advantageous in entrapping ligands such as nucleic acids, in particular aptamers. Typical cationic lipids may include DOTMA, N-[1-(2,3-dioleoyloxy)propyl]-N,N,N-trimethylammonium chloride; DOTAP, 1,2-dioleoyloxy-3-(trimethylammonio) propane; DOTB, 1,2-dioleoyl-3-(4'-trimethyl-ammonio)butanoyl-sn-glycerol, 1,2-diacyl-3-trimethylammonium-propane; 1,2-diacyl-3-dimethylammonium-propane; 1,2-diacyl-sn-glycerol-3-ethyl phosphocholine; and 3β-[N',N'-dimethylaminoethane)-carbamol]cholesterol-HCl.

In some embodiments, included in the lipid/surfactant at the surface are components with reactive groups that can be used to couple a targeting ligand or antibody and/or the ancillary substance useful for imaging or therapy.

Use of the Compositions in Magnetic Resonance Imaging

When used in magnetic resonance imaging, the compositions of the invention typically contain a paramagnetic ion within the chelating structure. In such applications, the inclusion of a spacer is particularly advantageous.

As set forth above, the function of the spacer is two-fold: first, by controlling the distance of the chelating agent and thereby the paramagnetic ion from the particles, the exposure of the paramagnetic ion to the hydrogen in the aqueous surroundings of the particles is controlled and thereby the relaxivity of the signal can be adjusted. Second, the coupling to spacer[1] is a cleavable group, thereby expediting the excretion of the chelated metal ion when its imaging function has been served.

Turning first to the effect on relaxivity, to maximize the relaxivities obtainable, the dimensions of the spacer are such that the paramagnetic ion is offset from the surface of the particle at a distance, of at least 5 or 10 Å. The average distance at which the paramagnetic ion is found from the surface may be between about 5-100 Å, preferably about 10-50 Å, and more preferably about 10-20 Å.

As used herein, the "surface" of the vehicle means the outer limit of the material comprising the particle at the location at which the chelator is coupled. Overall, the mean diameter of the particle itself is compared to the mean distance from the center where the paramagnetic ions reside. This should be at least a 5 Å difference preferably at least 10 Å.

The degree of offset can also be defined in terms of the resultant impact on the relaxivity imparted by the offset. The imparted relaxivity is dependent on the strength of the magnetic field; the relaxivity on a per particle basis is, of course, determined in part by the number of paramagnetic ions associated with the particle itself. At the arbitrarily chosen magnetic field strength of 0.47 T, the offset will be sufficient to enhance the relaxivity on a per ion basis at least 1.2 fold, preferably 1.5 fold, and more preferably 2.5 fold or 10 fold for m, and in similar amounts for $\tau_2$. At the arbitrarily chosen magnetic field of 1.5 T, the offsets will enhance these relaxivities by similar factors. At 4.7 T, preferably the enhancement of $\tau_1$ is at least 1.5 fold, preferably 2 fold and the enhancement of $\tau_2$ is at least two fold and preferably three fold, again, on a per ion basis. In terms of units of relaxivity per se, the offset is such that the value for $\tau_1$ in $(s*mM)^{-1}$ at 0.47 T is at least 20, and preferably 25, more preferably 30; at 1.5 T, these values would be at least 20, and preferably 30, and at 4.7 T, at least 10, and preferably 14. For $\tau_2$, the corresponding values at 0.47 T would be at least 20, preferably 30, and more preferably 35; at 1.5 T, at least 20, preferably 30; and at 4.7 T, at least 20, more preferably 40, and most preferably 60.

By appropriately coupling the chelating agents, substantial numbers of chelators and paramagnetic ions can be coupled to the particles. For the chelator containing a paramagnetic ion, typically, the particles contain at least 2,000 copies, typically at least 5,000, more typically at least 10,000 or 100,000 or 500,000. For targeting agents, only one or two, or several or more copies may be included. Variable numbers of drug molecules may be contained.

As a multiplicity of chelators containing paramagnetic ions are applied to the vehicles of the composition, considerably higher relaxivities can be obtained on a per particle basis. The fold increase in $\tau_1$ and $\tau_2$ on a per particle basis is, of course, similar to that with respect to the fold increase on a per ion basis. The present invention provides values of $\tau_1$ in units of $(s*mM)_y$ on a per particle basis at 0.47 T, of at least $1.8 \times 10^6$, preferably $2.0 \times 10^6$, and more preferably $2.5 \times 10^6$. At 1.5 T, these values are similar and at 4.7 T, relaxivity values for $\tau_1$ are at least $8 \times 10^5$, preferably $1 \times 10^6$, more preferably $1.1 \times 10^6$.

For $\tau_2$ at 0.47 T, the relaxivity is preferably at least $2 \times 10^6$, more preferably $2.5 \times 10^6$, and more preferably $3 \times 10^6$ in these units. At 1.5 T, the values for $\tau_2$ are at least $1.6 \times 10^6$, preferably $2.5 \times 10^6$, and more preferably $3 \times 10^6$. At 4.7 T, $\tau_2$ is at least $3 \times 10^6$, more preferably $4 \times 10^6$, and more preferably $5 \times 10^6$.

The offsetting is accomplished by spacing the dentate portion of the chelate through the spacer to the surface of the vehicle, as the phosphoglyceride associates with the lipophilic material at the surface.

Cleavable Spacers

In particular embodiments, the compounds of the present invention may comprise a cleavable spacer[1] so that the paramagnetic ion or radionuclide ion chelate can be dissociated from the particle or from lipids that compose part of the vehicle. It may be desirable to enhance excretion by liberating the chelate in a hydrophilic status to promote such excretion. In addition, the spacer[1] may contain one or more cleavage sites that either are activated externally, for example, by photoactivation, or which are continuously accessed by enzymes present in the cells or bloodstream. Examples of the former include specific linkages that are photoactivated, or cleaved by ultrasound, as is understood in the art. After imaging or therapy has been completed, the nanoparticles are subjected to electromagnetic energy or ultrasound as appropriate to effect cleavage. In the second instance, the spacer may be, or may include, peptides containing amino acid sequences that are susceptible to cleavage by circulating proteases or may include polysaccharides, themselves susceptible to such cleavage. Any combination of such cleavage sites may be included. The susceptibility of the spacer or tether to cleavage thus enhances excretion and diminishes potential toxicity of the paramagnetic ion.

If continuous degradation is employed, the rate may be modulated by selecting spacers according to the available enzymatic activities and by supplying a desired number of cleavage sites. However, it is well known that any peptide circulating in the bloodstream is ultimately destroyed due to circulating proteases; similarly, polysaccharides are subject to cleavage by endogenous enzymes.

Methods of Preparation

The precise process for preparation of the compositions of the invention is variable, and depends on the nature of the particulate vehicle. In general, however, lipophilic particle surfaces associate with the lipophilic $R^2$ groups in the compounds having formula (1), (1A) and (1B). In one particular embodiment, the process involves mixing a liquid fluorocarbon compound that forms the core of a nanoparticle and the components of a lipid/surfactant coating for that particle in an aqueous suspension, microfluidizing, and, if desired, harvesting and sizing the particles. The components to be coupled can be included in the original mixture by virtue of their association with the components of the lipid/surfactant coating, or the coupling to additional moieties can be conducted after the particles are formed.

Kits

The emulsions of the invention may be prepared and used directly in the methods of the invention, or the components of the emulsions may be supplied in the form of kits. The kits may comprise a pre-prepared targeted composition containing all of the desired ancillary materials in buffer or in lyophilized form. Alternatively, the kits may include a form of the emulsion which lacks the compound of any of formula (1), (1A), and (1B) and/or a targeting agent, each of which may be supplied separately. If a targeting agent is to be directly bound, the emulsion will contain a reactive group, such as a maleimide group, which, when the emulsion is mixed with the targeting agent, effects the binding of the targeting agent to the emulsion itself. A separate container may also provide additional reagents useful in effecting the coupling. Alternatively, the emulsion may contain reactive groups which bind to linkers coupled to the desired component to be supplied separately which itself contains a reactive group. A wide variety of approaches to constructing an appropriate kit may be envisioned. Individual components which make up the ultimate emulsion may thus be supplied in separate containers, or the kit may simply contain reagents for combination with other materials which are provided separately from the kit itself.

A non-exhaustive list of combinations might include: emulsion preparations that contain, in their lipid-surfactant layer, an ancillary component such as a fluorophore or chelating agent and reactive moieties for coupling to a targeting agent; the converse where the emulsion is coupled to targeting agent and contains reactive groups for coupling to an ancillary material; emulsions which contain both targeting agent and a chelating agent but wherein the metal to be chelated is either supplied in the kit or independently provided by the user; preparations of the nanoparticles comprising the surfactant/lipid layer where the materials in the lipid layer contain different reactive groups, one set of reactive groups for a targeting agent and another set of reactive groups for an ancillary agent; preparation of emulsions containing any of the foregoing combinations where the reactive groups are supplied by a linking agent.

Applications

The emulsions and kits for their preparation are useful in the methods of the invention which include imaging of tissues and providing therapeutic agents.

The magnetic resonance imaging contrast agents of the present invention may be used in a similar manner as other MRI agents as described in U.S. Pat. No. 5,155,215; U.S. Pat. No. 5,087,440; Margerstadt, et al., *Magn. Reson. Med.* (1986) 3:808; Runge, et al., *Radiology* (1988) 166:835; and Bousquet, et al., *Radiology* (1988) 166:693. Other agents that may be employed are those set forth in U.S. patent publication 2002/0127182 which are pH sensitive and can change the contrast properties dependent on pulse. Generally, sterile aqueous solutions of the contrast agents are administered to a patient intravenously in dosages ranging from 0.01 to 1.0 mmoles per kg body weight.

When the compositions of the invention contain targeted delivery vehicles, suitable targets include any tissue of interest, including tumor tissue, atherosclerotic plaques, blood clots, and the like. The choice of targeting agent will, of course, depend on the nature of the target itself. For example, to target atherosclerotic plaques or blood clots, antifibrin antibodies are appropriate as are peptidomimetics that interact with avid integrins. Suitable targeting agents for tumors may include antibodies prepared against tumor associated antigens or prepared with respect to the organ hosting the tumor. Imaging of particular organs would employ targeting agents that interact with receptors or other characteristic moieties associated with the target itself.

The following examples are intended to illustrate but not to limit the invention.

Preparation A

Nanoparticle Preparation

Paramagnetic nanoparticles were produced in a modification of the procedure described by Lanza, G, et al., *Circulation* (1996) 94:3334-3340. Briefly, the emulsions comprised 40% (v/v) perfluorooctylbromide (PFOB; MMM, St. Paul, Minn.), 2% (w/v) safflower oil, 2% (w/v) of a surfactant co-mixture, 1.7% (w/v) glycerin and water representing the balance. The surfactant co-mixture included 63 mole % lecithin (Avanti Polar Lipids, Inc., Alabaster, Ala.), 15 mole % cholesterol (Sigma Chemical Co., St. Louis, Mo.), 2 mole % dipalmitoyl-phosphatidylethanolamine (Avanti Polar Lipids, Inc., Alabaster, Ala.), and 20 mole % of the paramagnetic lipophilic chelate (e.g., DOTA and DOTA derivatives). The surfactant components were dissolved in chloroform, evaporated under reduced pressure, dried in a 50° C. vacuum oven overnight and dispersed into water by sonication. The suspension was pre-emulsified in a blender with PFOB, safflower oil and distilled deionized water for 30 to 60 seconds and then emulsified in a M110S Microfluidics emulsifier (Microfluidics, Newton, Mass.) at 20,000 PSI for four minutes. The completed formulation was placed in crimp sealed vials and blanketed with nitrogen. Particle sizes were determined in triplicate at 37° C. with a laser light scattering submicron particle sizer (Malvem Instruments, Malvern, Worcestershire, UK).

EXAMPLE 1

Synthesis of Amide Gd Ligand

Scheme 1 illustrates a synthetic scheme for preparing an amide containing ligand for gadolinium. As shown in Scheme 1, reaction of a suitable mono-protected diamine 1 (i.e., 1-(t-butoxycarbonylamino)-6-aminohexane) with a α-halo acetylhalide 2 in the presence of added base (i.e., i-Pr$_2$NEt) gives the α-halo amide 3. Nucleophilic displacement of the α-halo amide with the macrocyclic tetramine 4 (i.e., 1,4,7, 10-tetraazacyclododecane) gives the mono-functionalized macrocycle 5 in the presence of added base (i.e., i-Pr$_2$NEt). Further alkylation of the remaining nitrogens in the macrocycle with α-halo-benzyl acetate, 6, in the presence of a suitable base (i.e., i-Pr$_2$NEt) gives the tetrafunctional derivative 7. Removal of the t-butoxycarbonyl group with a suitable acid (i.e., trifluoroacetic acid) gives the amine 8 after neutralization.

Conversion of the amine 8 to its corresponding isocyanate is achieved by, first formation of the amine carbamate salt by addition of carbon dioxide and base (i.e., Et$_3$N) at temperatures less than ambient (i.e., −10C) in a suitable solvent (i.e., CH$_2$Cl$_2$). This carbamate salt is then converted to the isocyanate by the addition of methanesulfonic acid anhydride (other agents may substitute for the methanesulfonic acid anhydride to include; however, not limited to, benzenesulfonic acid anhydride, toluenesulfonic acid anhydride, o-sulfobenzoic acid anhydride, trifluoroacetic acid anhydride, $P_2O_5$, $POCl_3$, $SOCl_2$). Isolation of the isocyanate from resulting salts is achieved by extraction of the organic reaction solvent with water giving 9 which can be further purified by techniques known to those skilled in the art.

Urea formation by the addition of an amino lipid 10 (i.e., phosphatidylcholine) gives 11. Hydrogenolysis of the benzyl esters in 11 gives the desired final product 12 as a material suitable as a ligand for gadolinium.

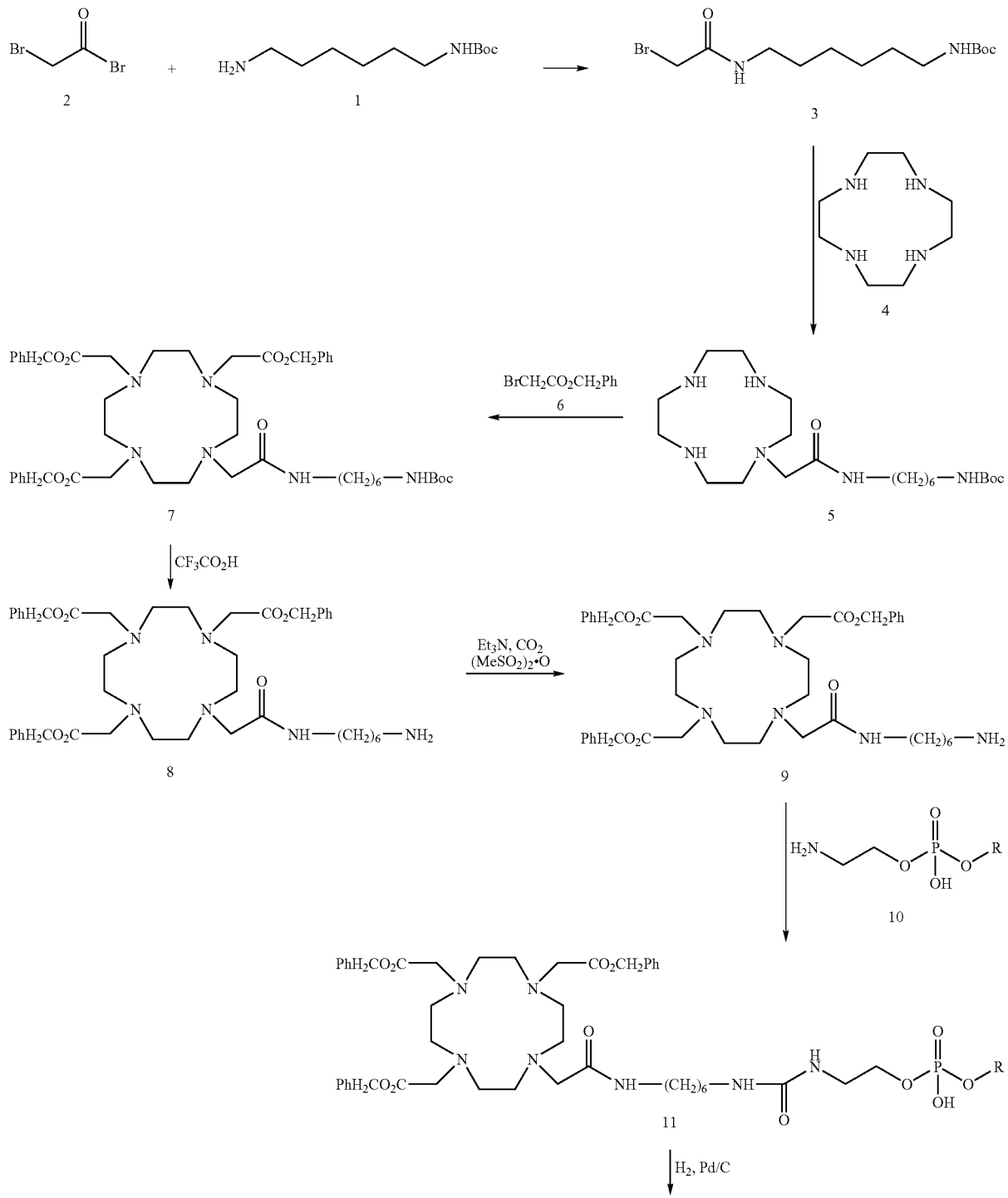

SCHEME 1:
Synthesis of amide containing ligand for Gadolinium

-continued

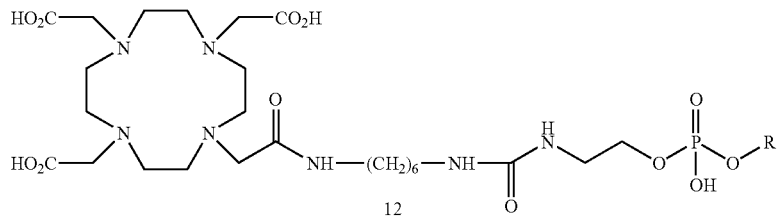

EXAMPLE 2

Introduction of Gadolinium Ion

Gadolinium ion may be introduced into the chelate either by initially metalating DOTA before or during the preparation of the compound of formula (1) or metalating after synthesis.

For example, premetalation of DOTA or DOTA'-CONR$^1$ (spacer$^1$) NR$^1$H is carried out in aqueous solution using a stoichiometric amount of GdCl$_3$. The reaction mixture is lyophilized to dryness and used without further purification prior to conjugation with PE or triglycyl-PE. As salts carried onto the final conjugation negatively affect the coupling chemistry, they are removed by aqueous rinses of the dried reaction mixture.

Gd$_2$O$_3$ may be used in place of GdCl$_3$ to produce a "salt free" metal complex, by boiling the solution containing Gd$_2$O$_3$ for an extended period of time in MeOH/chloroform.

Postmetalation of the compound of formula (1) is carried out with GdCl$_3$ in a chloroform methanol mixture with boiling or in anhydrous DMF.

EXAMPLE 3

Preparation of Emulsions

The conjugates of formula (1) are associated with nanoparticles prepared as in Preparation A. Each particle will contain approximately 33,000 Gd$^{3+}$ chelates.

EXAMPLE 4

Preparation of another Embodiment of a (DOTA-Amide) Ligand

Scheme 2 below illustrates the synthesis of another embodiment of the invention.

Scheme 2

STEP 1

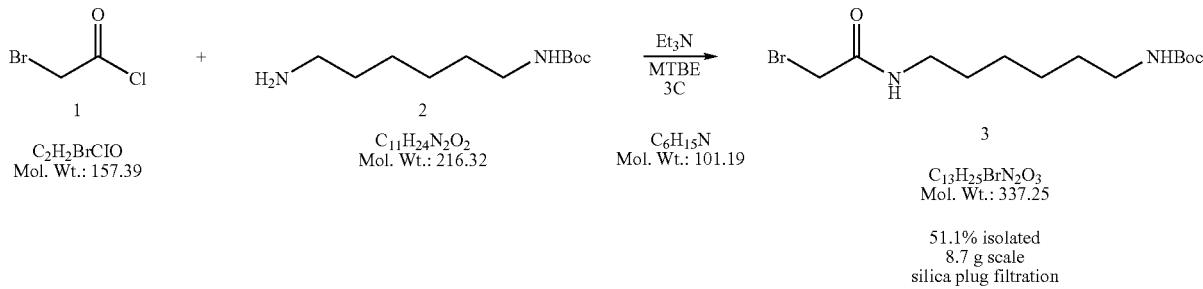

STEP 2

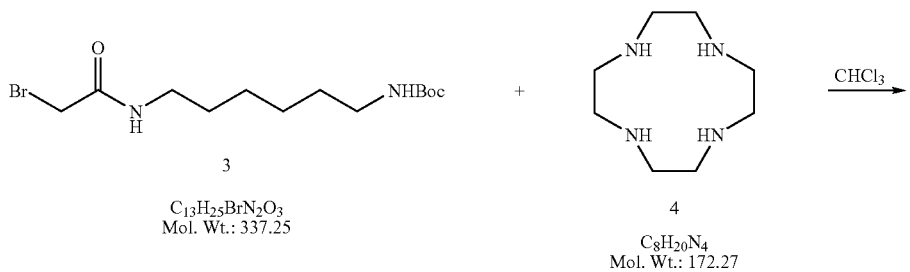

-continued
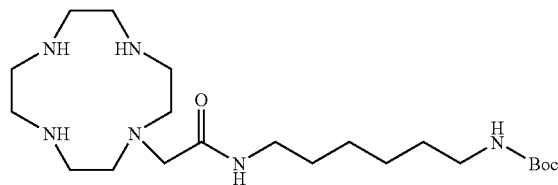
5
C$_{21}$H$_{44}$N$_6$O$_3$
Mol. Wt.: 428.61
Quantitative recovery
No purificataion
STEP 3
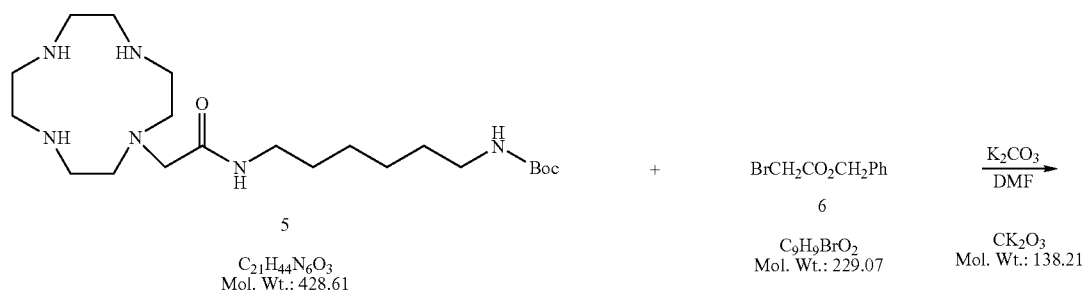
5
C$_{21}$H$_{44}$N$_6$O$_3$
Mol. Wt.: 428.61
6
C$_9$H$_9$BrO$_2$
Mol. Wt.: 229.07
CK$_2$O$_3$
Mol. Wt.: 138.21
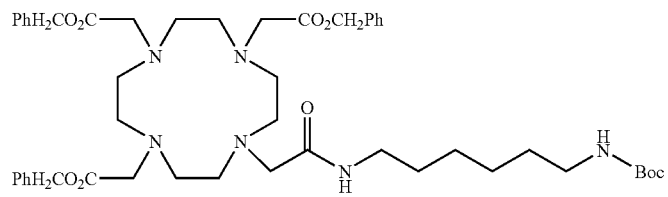
7
C$_{48}$H$_{68}$N$_6$O$_9$
Mol. Wt.: 873.09
46% isolated
9 g scale
Silica column
STEP 4
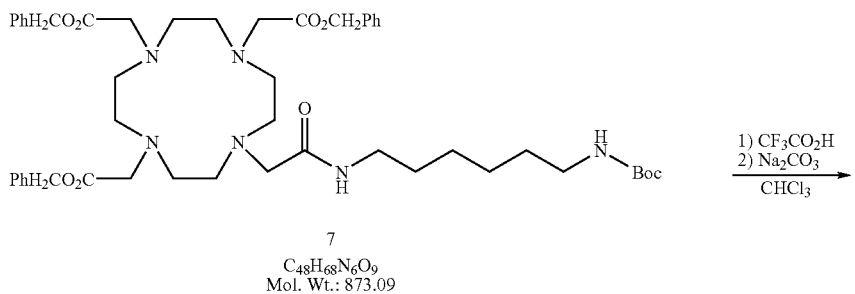
7
C$_{48}$H$_{68}$N$_6$O$_9$
Mol. Wt.: 873.09

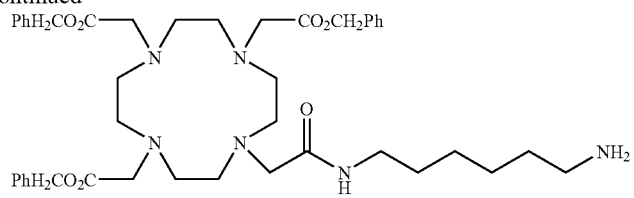
8
C$_{43}$H$_{60}$N$_6$O$_7$
Mol. Wt.: 772.97
Quantitative on 4 g scale
No purification
STEP 5
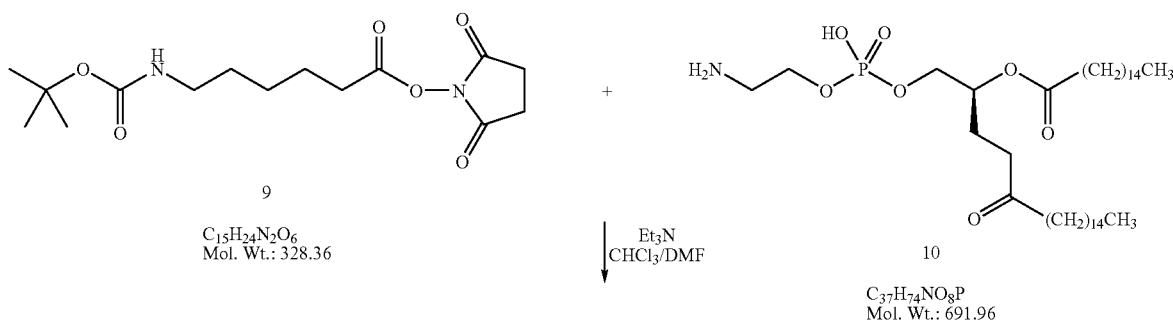
9
C$_{15}$H$_{24}$N$_2$O$_6$
Mol. Wt.: 328.36
10
C$_{37}$H$_{74}$NO$_8$P
Mol. Wt.: 691.96
Et$_3$N
CHCl$_3$/DMF
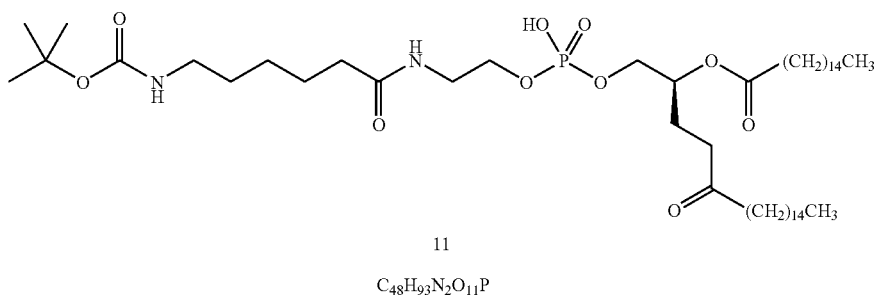
11
C$_{48}$H$_{93}$N$_2$O$_{11}$P
Mol. Wt.: 605.23
STEP 6
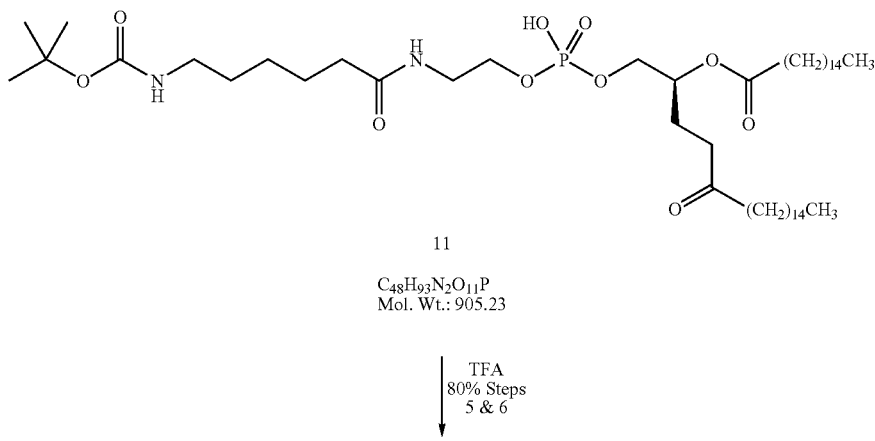
11
C$_{48}$H$_{93}$N$_2$O$_{11}$P
Mol. Wt.: 905.23
TFA
80% Steps
5 & 6

-continued
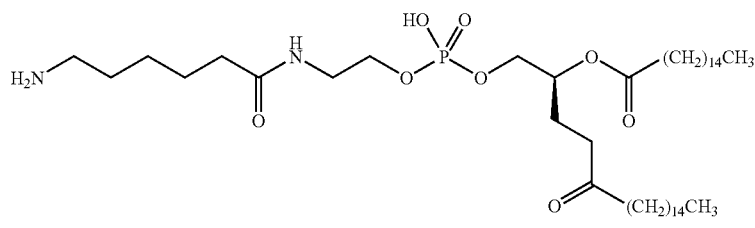
12
C₄₃H₈₅N₂O₉P
Mol. Wt.: 805.12
STEP 7
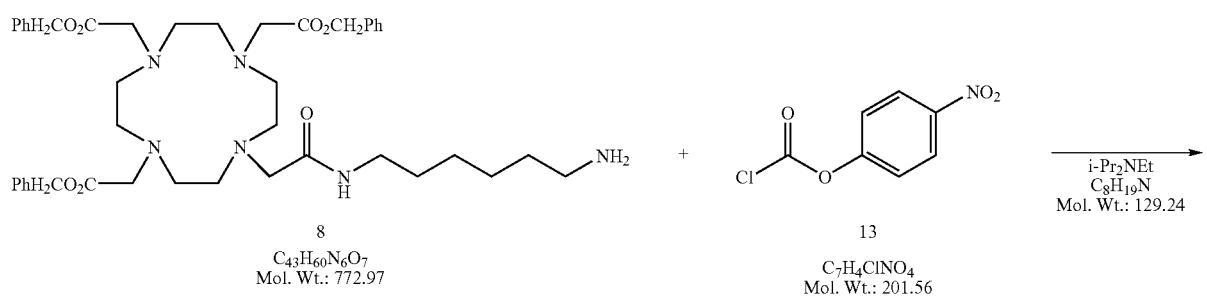
STEP 8
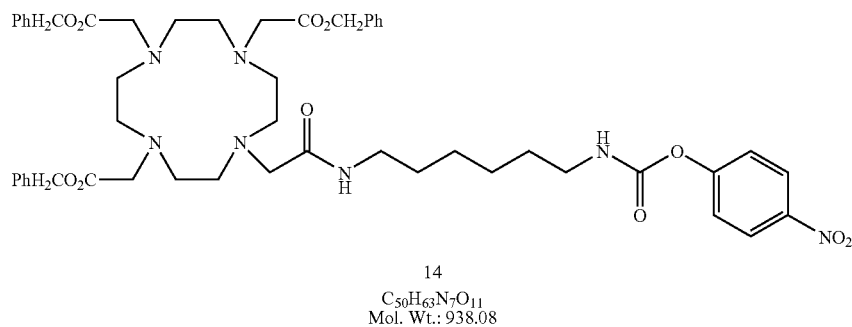
14
C₅₀H₆₃N₇O₁₁
Mol. Wt.: 938.08
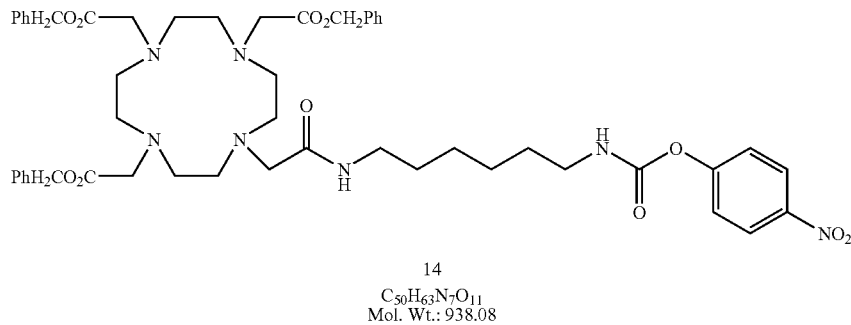
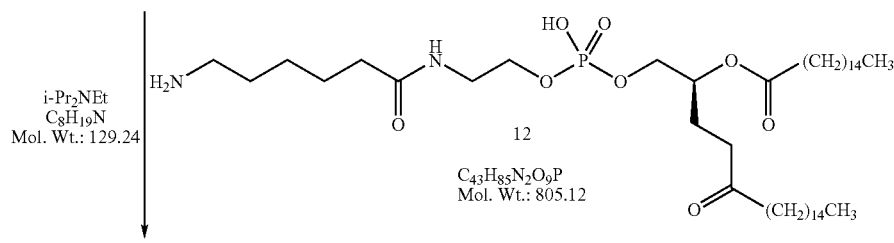
12
C₄₃H₈₅N₂O₉P
Mol. Wt.: 805.12

-continued
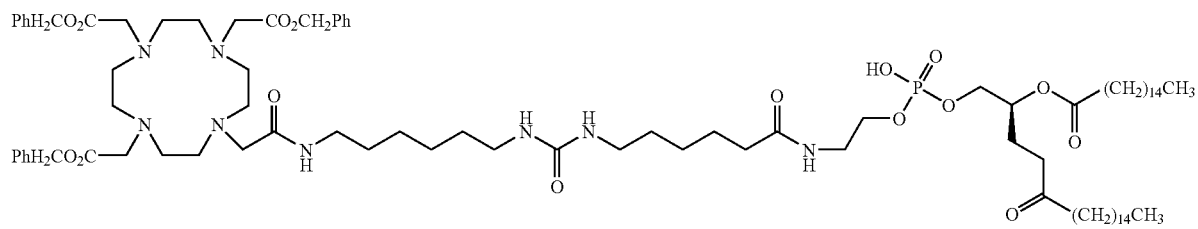
15
C₈₇H₁₄₃N₈O₁₇P
Mol. Wt.: 1604.08
STEP 9
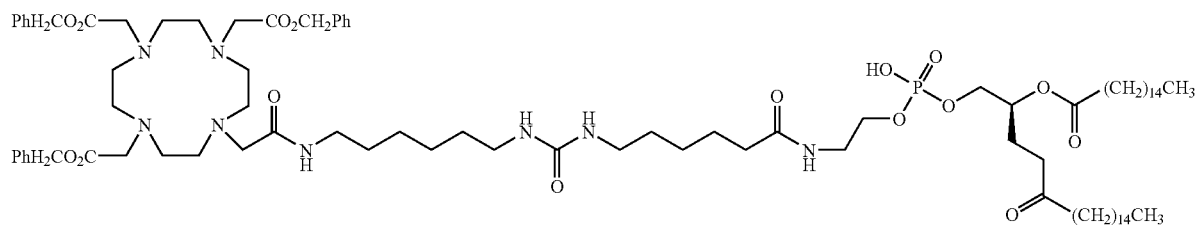
15
C₈₇H₁₄₃N₈O₁₇P
Mol. Wt.: 1604.08
H₂, Pd/C
EtOH
73%
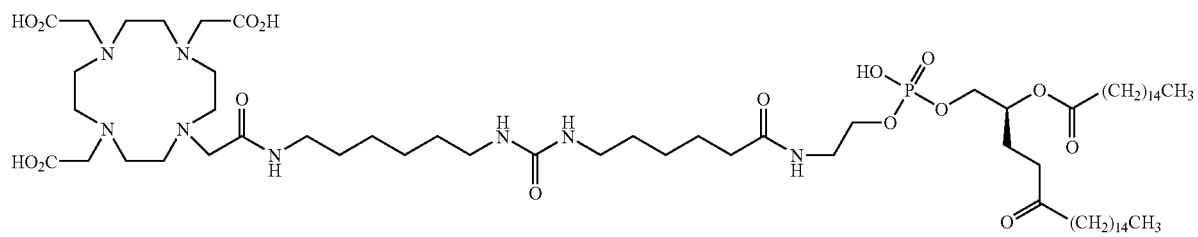
16
C₆₆H₁₂₅N₈O₁₇P
Mol. Wt.: 1333.72

STEP 10

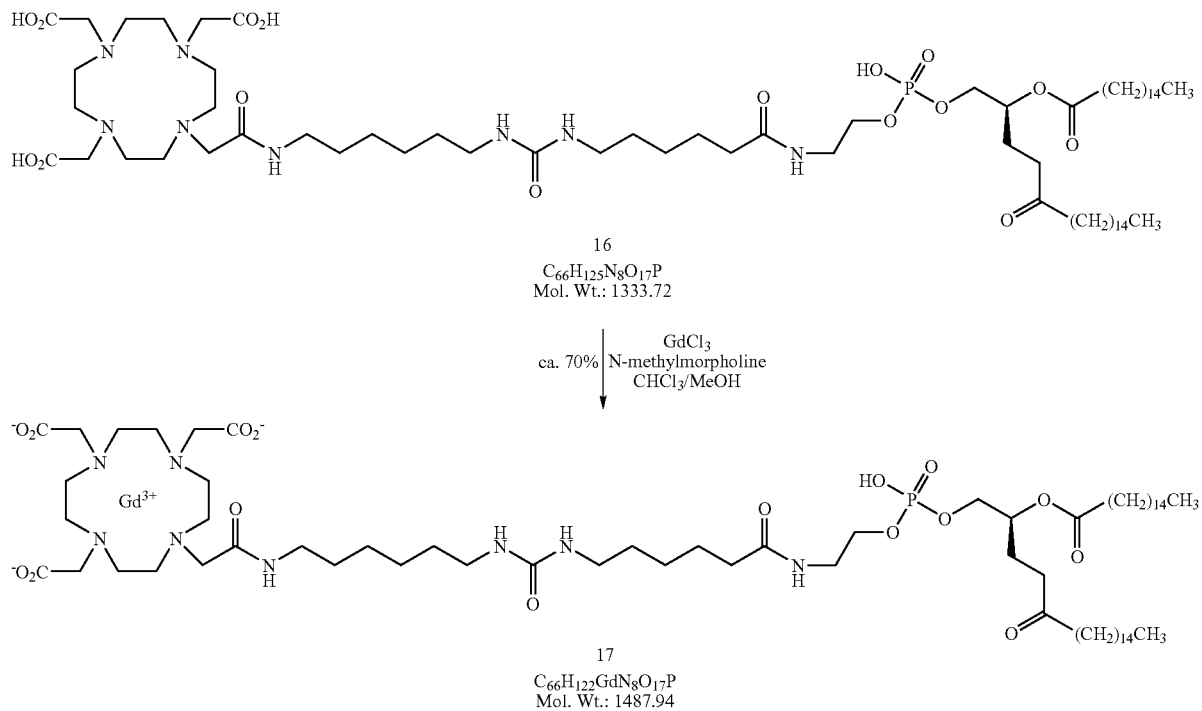

16
C$_{66}$H$_{125}$N$_8$O$_{17}$P
Mol. Wt.: 1333.72 ca. 70% | GdCl$_3$, N-methylmorpholine, CHCl$_3$/MeOH

17
C$_{66}$H$_{122}$GdN$_8$O$_{17}$P
Mol. Wt.: 1487.94

Experimental

STEP 1

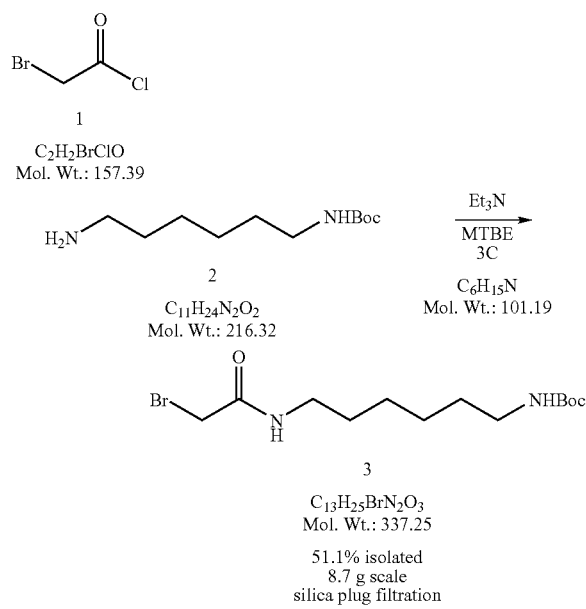

1
C$_2$H$_2$BrClO
Mol. Wt.: 157.39

2
C$_{11}$H$_{24}$N$_2$O$_2$
Mol. Wt.: 216.32

Et$_3$N / MTBE / 3C

C$_6$H$_{15}$N
Mol. Wt.: 101.19

3
C$_{13}$H$_{25}$BrN$_2$O$_3$
Mol. Wt.: 337.25

51.1% isolated
8.7 g scale
silica plug filtration

| Substrate | g/mol | g/mL | Amt | Mmol | Source |
|---|---|---|---|---|---|
| N-Boc-1,6-hexanediamine, 2 | 216.32 | | 10.85 g | 50.2 | Lancaster |
| Bromoacetyl chloride, 1 | 157.39 | 1.89 | 4.35 mL | 52.2 | Fluka |
| TEA | 101.19 | 0.726 | 7.3 mL | 52.4 | Aldrich |
| MTBE | | | 175 mL | | Aldrich |
| 3 | 337.25 | | | | |

Under a nitrogen atmosphere, a mechanically stirred mixture of 1-(tert-butoxycarbonyl)-1,6-hexanediamine, 2, (10.85 g; 50.2 mmol) and triethylamine (7.3 mL; 52.4 mmol) in 100 mL anhydrous methyl tert-butyl ether was cooled in an ice bath to 3° C. A solution of bromoacetyl chloride, 1, (4.35 mL; 52.2 mmol) in 50 mL anhydrous methyl tert-butyl ether was added dropwise at 3-9° C. over a period of 77 minutes. The tan slurry was stirred overnight at ambient temperature under nitrogen.

After 15 hrs, the tan slurry was partitioned between ethyl acetate (150 mL) and water (100 mL). The separated organic layer was washed successively with ice-cold 2.5% aqueous HCl (100 mL), saturated NaHCO$_3$ (100 mL) and saturated brine (100 mL). The organic layer was dried over Na$_2$SO$_4$ and filtered to give a brown filtrate. The filtrate was concentrated on a rotary evaporator at 45° C. to give a brown oil. This oil was slurried in hexane (10 mL) and reconstituted on the rotary evaporator to give a brown sticky solid; 13.25 g. The solid was dried in the vacuum oven at 35° C. (10:15 am) for 145 minutes; 12.9 g. The solid was soluble in hot ether, hot toluene and in CH$_2$Cl$_2$, and recrystallized from CH$_2$Cl$_2$ in white clusters with orange oil on bottom.

The solid was dissolved in hot ethyl acetate (30 mL) and diluted with hexane (30 mL). The solution was suction filtered through a pad of pre-wetted Merck grade 9385 silica gel (50 g) topped with a piece of filter paper. The silica gel was washed with 1:1 ethyl acetate:hexane (1,000 mL). Four fractions of 250 mL each were collected and analyzed by TLC. Fractions containing desired product were combined and concentrated on a rotary evaporator at 45° C. to give a light peach solid; 11.6 g. This solid was dissolved in dichloromethane (50 mL), diluted with hexane (200 mL) and swirled vigorously to crystallize solid.

The heavy slurry was suction filtered and washed with hexane to give a beige solid; 11.8 g. The solid was dried in vacuum oven at 35° C. for 105 min giving 8.65 g desired product 3 (51%).

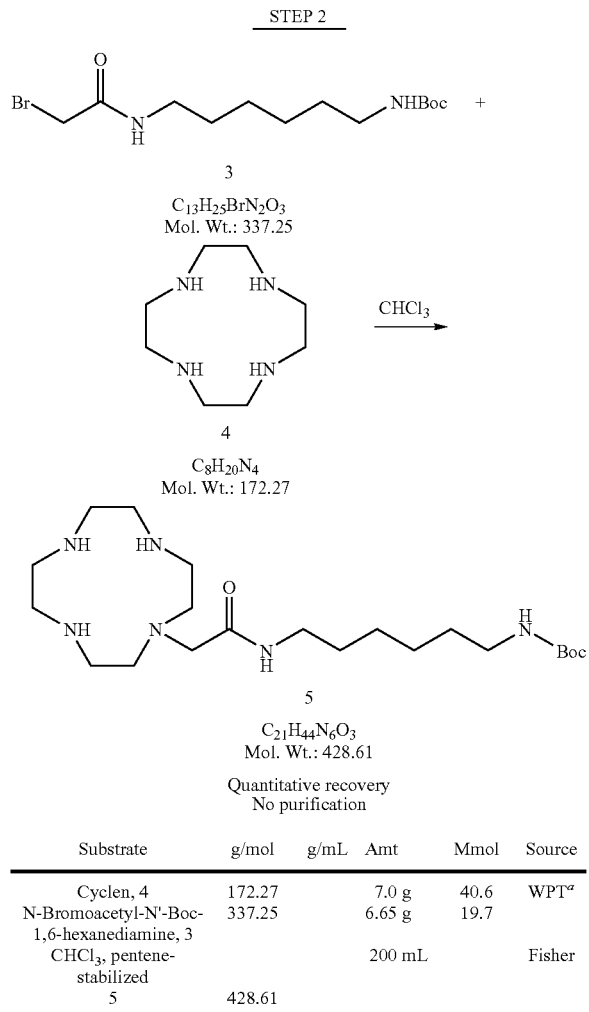

| Substrate | g/mol | g/mL | Amt | Mmol | Source |
|---|---|---|---|---|---|
| Cyclen, 4 | 172.27 | | 7.0 g | 40.6 | WPT[a] |
| N-Bromoacetyl-N'-Boc-1,6-hexanediamine, 3 | 337.25 | | 6.65 g | 19.7 | |
| CHCl$_3$, pentene-stabilized | | | 200 mL | | Fisher |
| 5 | 428.61 | | | | |

[a]Wilmington Pharma Tech Co.

Under a nitrogen atmosphere, a magnetically stirred solution of cyclen, 4 (7.0 g; 40.6 mmol) in pentene-stabilized chloroform (100 mL) was treated dropwise with a solution of N-bromoacetyl-N'-(tert-butoxycarbonyl)-1,6-hexanediamine (6.65 g; 19.7 mmol) in 100 mL chloroform at room temperature over a period of 6.5 hrs. The hazy mixture was stirred overnight at room temperature.

After 17 hrs at room temperature under nitrogen, an aliquot (0.1 mL) of the tan slurry was diluted in 20 mL 50% aqueous acetonitrile containing 0.05% formic acid. LC/MS showed the desired product, the excess cyclen and no detectable starting bromide. The reaction slurry was washed with 1N aqueous Na$_2$CO$_3$ (100 mL) and with water (165 mL×4). LC/MS showed negligible levels of cyclen in the baseline. However, another wash with water (165 mL) was conducted. After drying over Na$_2$SO$_4$, the light amber chloroform filtrate was concentrated on a rotary evaporator at 40° C. to give an amber oil; 12.8 g. This oil was evaporated on a Kugelrohr at 50° C. and 0.1-0.4 torr for 100 min. to give a viscous amber oil; 9.3 g then at ambient overnight, 9.2 g 5 (108.9%).

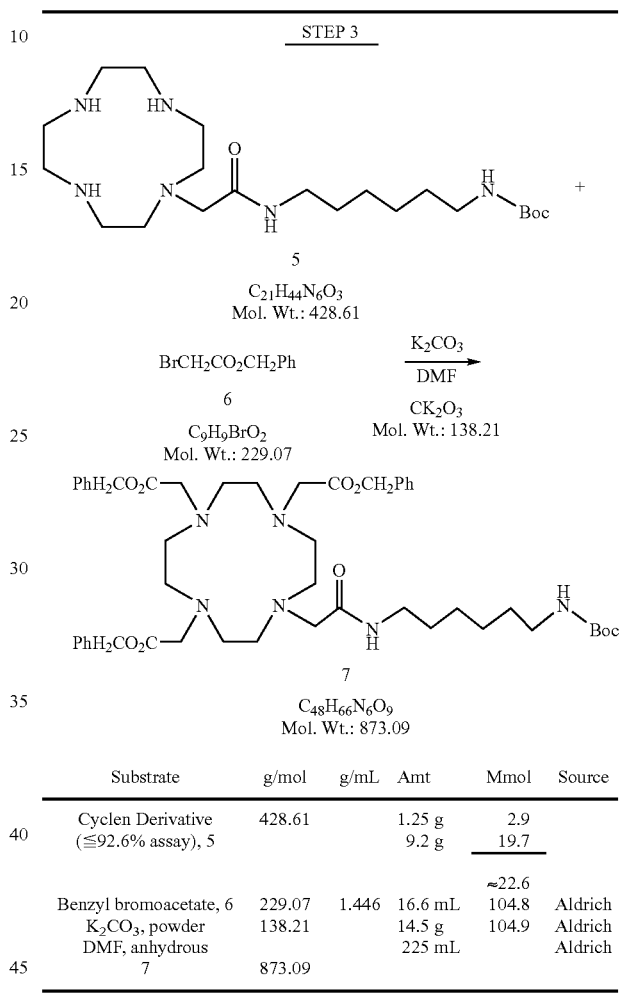

| Substrate | g/mol | g/mL | Amt | Mmol | Source |
|---|---|---|---|---|---|
| Cyclen Derivative (≦92.6% assay), 5 | 428.61 | | 1.25 g<br>9.2 g | 2.9<br>19.7 | |
| | | | | ≈22.6 | |
| Benzyl bromoacetate, 6 | 229.07 | 1.446 | 16.6 mL | 104.8 | Aldrich |
| K$_2$CO$_3$, powder | 138.21 | | 14.5 g | 104.9 | Aldrich |
| DMF, anhydrous | | | 225 mL | | Aldrich |
| 7 | 873.09 | | | | |

Under a nitrogen atmosphere, a mechanically stirred mixture of powdered potassium carbonate (14.5 g; 104.9 mmol) and crude [6-(2-1,4,7,10-Tetraaza-cyclododec-1-yl-acetylamino)-hexyl]-carbamic acid tert-butyl ester 5 (10.45 g; ≈22.6 mmol) in 225 mL anhydrous N,N-dimethylformamide was treated with neat benzyl bromoacetate (16.6 mL; 104.8 mmol) in one portion. A slight exotherm immediately raised the temperature to 32° C. The resulting slurry was stirred at ambient temperature under nitrogen. After 3 hrs, an aliquot (2 drops) was diluted in 10 mL 50% aqueous acetonitrile containing 0.05% formic acid. LC/MS showed the desired product as the major component plus DMF, unreacted benzyl bromoacetate and an unknown. There was no evidence of starting monoalkylated cyclen or any related intermediates. After 3.5 hrs at ambient temperature, the slurry was mixed with 5% aqueous NaCl (600 mL) and extracted with ethyl acetate (600 mL×2). The combined ethyl acetate layers were washed with 5% aqueous brine (600 mL×3), dried over Na$_2$SO$_4$, filtered and concentrated on a rotary evaporator at 25-40° C. to give an amber oil; 29.4 g. The amber oil was evaporated on a Kugelrohr at 50° C. and 0.2-0.4 torr for 30 minutes with a slight weight drop; 26.85 g.

The oil was dissolved in chloroform (30 mL) and added to a pre-wetted Biotage 75 L silica gel column. The sample was chased onto the column with additional chloroform (30 mL×3). The column was then eluted with a step gradient of methanol in chloroform as follows (volume, vol % methanol): (5,000 mL of 0%, 5,000 mL of 1%, 5,000 mL of 2%, 5,000 mL of 3%, 5,000 mL of 4%). Due to the lack of chloroform, dichloromethane was substituted and the step gradient of methanol in dichloromethane continued as the following: 5,000 mL of 5% and 5,000 mL of 6%.

The combined fractions were concentrated on a rotary evaporator at 35° C. and then on a Kugelrohr at 50° C. and 0.2 torr to give a beige, foamy glass; 9.15 g 7 (46.4%).

A magnetically stirred solution of 4,7-bis-benzyloxycarbonylmethyl-10-[(6-tert-butoxycarbonylamino-hexylcarbamoyl)-methyl]-1,4,7,10-tetraaza-cyclododec$^{-1}$-yl}-acetic acid benzyl ester 7 (4.65 g; 5.33 mmol) in 52 mL dichloromethane was treated with neat trifluoroacetic acid (52 mL; 675 mmol). The mixture was stirred at room temperature under a $CaSO_4$ drying tube. After 60 minutes, the light yellow solution was concentrated on a rotary evaporator at room temperature to give a viscous light yellow oil; 13.75 g. This oil was dissolved in chloroform (200 mL) and washed with 1N aqueous $Na_2CO_3$ (150 mL) to give a pH of 8-9 for the cloudy water layer. The chloroform layer was then washed with water (100 mL). The milky chloroform layer was dried over $Na_2SO_4$, filtered and concentrated on a rotary evaporator at room temperature with a Buchi pump to give a light amber

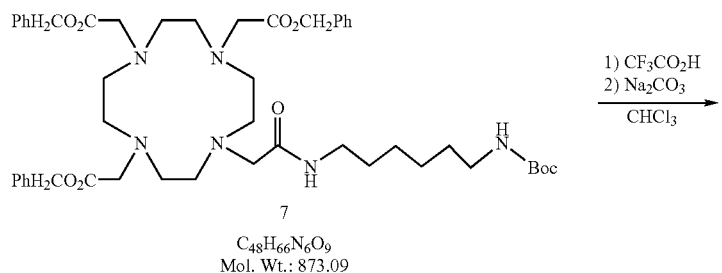

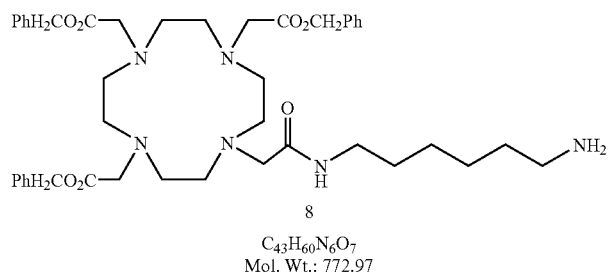

| Substrate | g/mol | g/mL | Amt | Mmol | Source |
|---|---|---|---|---|---|
| Boc-protected cyclen derivative, 7 | 873.09 | | 4.65 g | 5.33 | |
| TFA | 114.02 | 1.48 | 52 mL | 675 | Aldrich |
| $CH_2Cl_2$ | | | 52 mL | | Fisher |
| 8 | 772.97 | | | | | foamy gum; 4.9 g. This material was evaporated on a Kugelrohr at room temperature and 0.05 torr for 65 minutes to give a beige foamy glass; 4.15 g, 8 (100.7%).

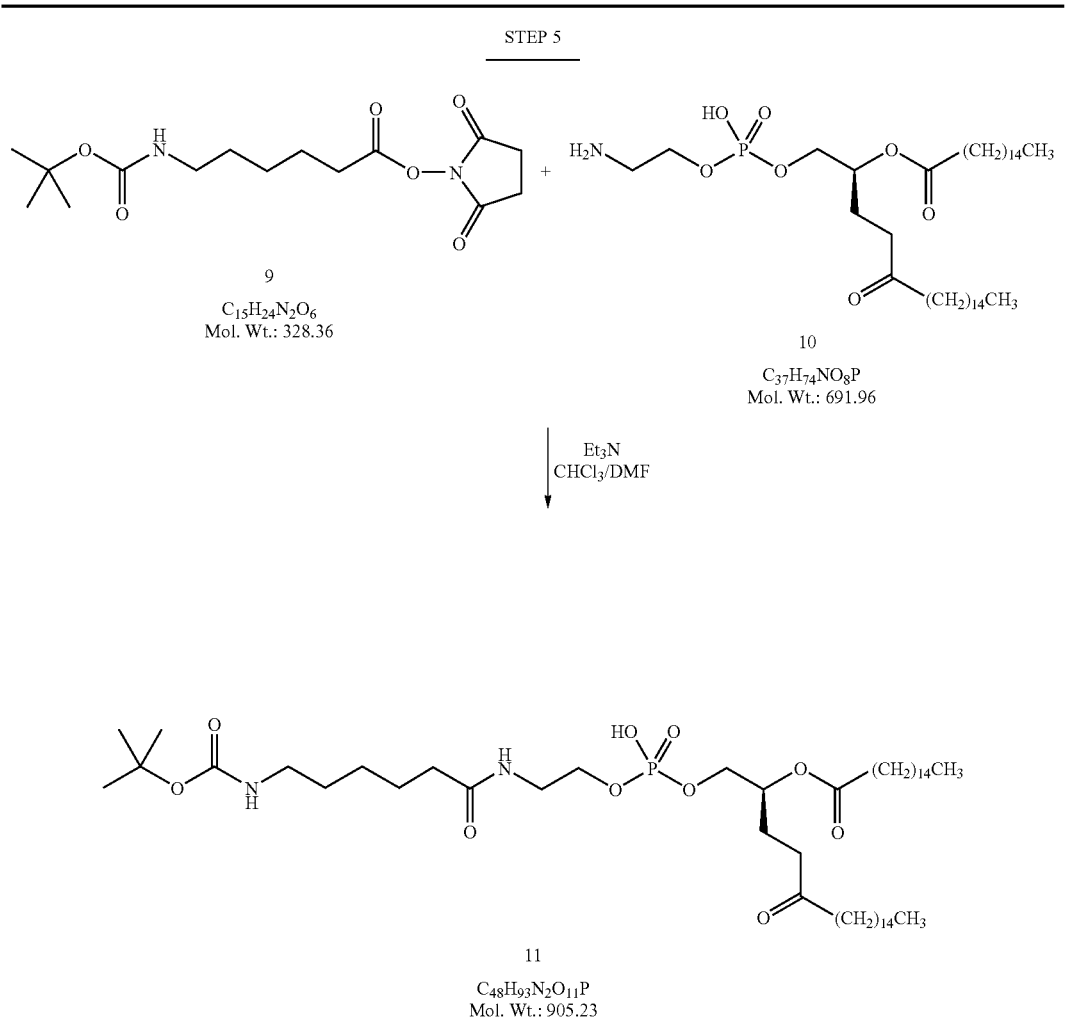

STEP 5

| Materials | Supplier | MW | n [mmol] | Eq. | Amt. |
| --- | --- | --- | --- | --- | --- |
| N-hydroxysuccinamide BOC-6-amino-hexanoate, 9 | Fluka | 328.36 | 12.18 | 1.05 | 4.0 g |
| DPPE, 10 | Lipoid | 691.96 | 11.56 | 1 | 8.0 g |
| Et$_3$N | Sigma Aldrich | | 45.5 | 3.9 | 4.6 g |

A 250 mL RB flask was charged with 4.0 g (12.18 mmol, FW=328.36, Fluka) of the active ester, 9, 8.0 g (11.56 mmol, FW=691.96, Lipoid) of DPPE, 10, and 110 mL of 1:1 (v:v) CHCl$_3$:DMF. To this slurry was then added 4.6 g Et$_3$N (45.5 mmol, FW=101, Fluka) and the reaction mixture was heated to 50° C. under Argon for 3 h (reaction became homogeneous after ca. 90 min). The reaction mixture was allowed to cool to ambient temperature overnight. The crude reaction was concentrated in vacuo at 40° C. The semi-solid residue was then dissolved in 200 mL CH$_2$Cl$_2$ and extracted 2×100 mL Milli-Q water (this extraction caused an emulsion to form which did not fully break on sitting, the aqueous layer remained cloudy). The aqueous layers were back extracted with 100 mL CH$_2$Cl$_2$. The CH$_2$Cl$_2$ layers were combined and dried over Na$_2$SO$_4$, filtered and then concentrated in vacuo at 25° C. leaving a white sticky solid, 11 (100%, 10.5 g, 11.6 mmol FW=905.23).

STEP 6

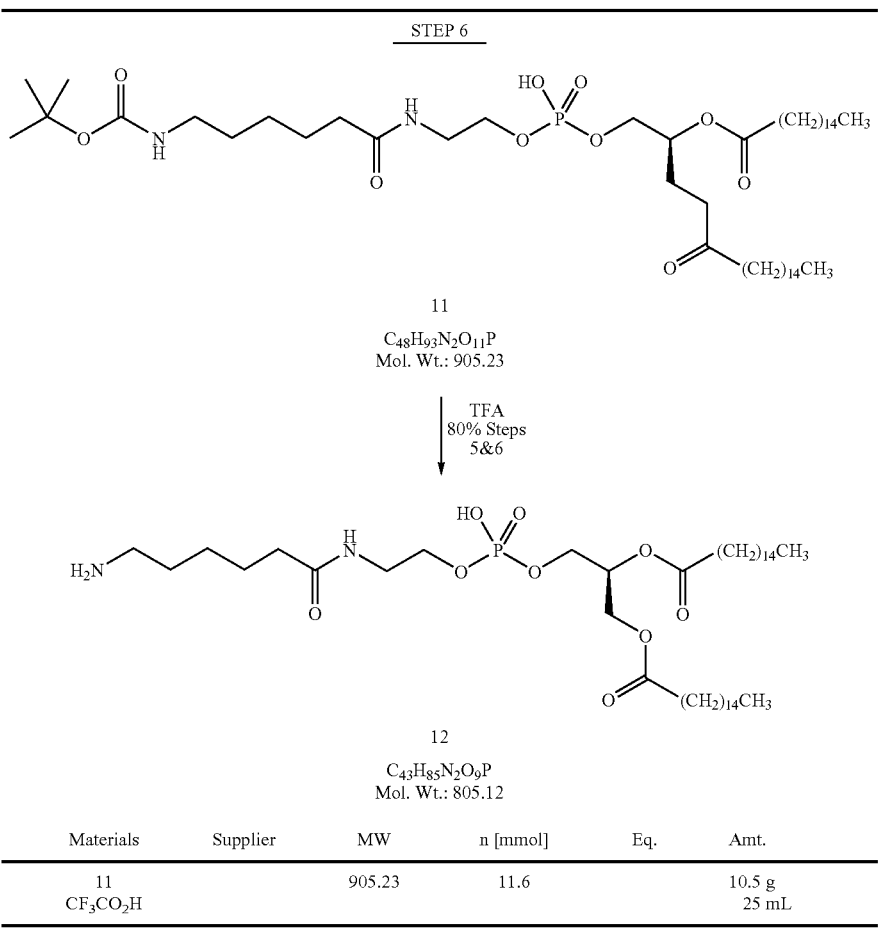

To a 250 mL RB flask was added 10.5 g of Boc-Cap-DPPE, 11 (11.6 mmol, FW=905.23) and 25 mL neat $CF_3CO_2H$ (vigorous evolution of gas upon addition of TFA). The solution was allowed to stir at ambient temperature for 3 hr. To the solution was added 50 mL $CH_2Cl_2$ and the reaction mixture concentrated in vacuo. A second 50 mL of $CH_2Cl_2$ was added and this was concentrated in vacuo to a clear oil.

The oil from above was dissolved in 200 mL $CH_2Cl_2$, then extracted with 2×125 mL 0.5 M aq. $Na_2CO_3$ (first 125 mL, vigorous gas evolution). The pH of the second aqueous layer remained basic. The aqueous layers were back extracted with 100 mL $CH_2Cl_2$ (aqueous layers remained milky white). The $CH_2Cl_2$ layers were combined, dried over $Na_2SO_4$, filtered and concentrated in vacuo leaving a flaky white solid, 12 (7.47 g, 9.27 mmol, 80%).

STEP 7

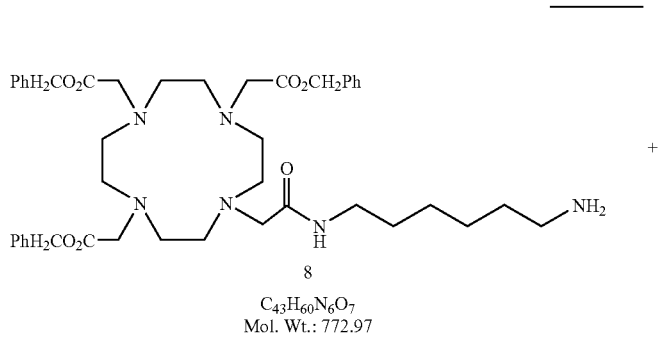

-continued
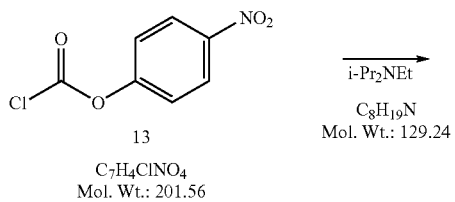
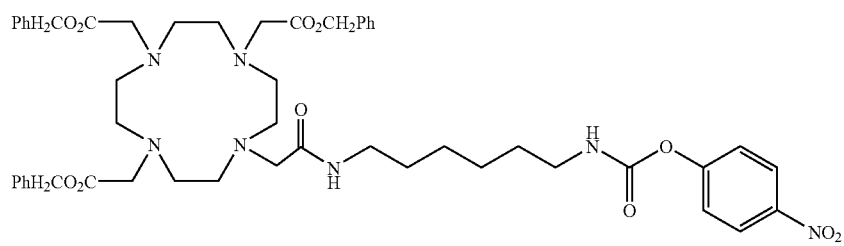
STEP 8
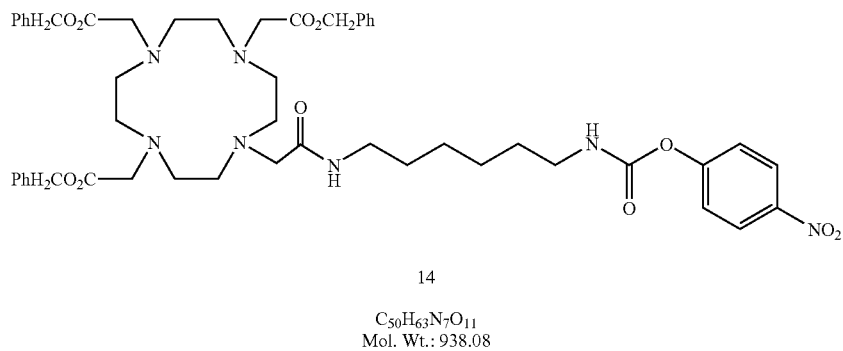
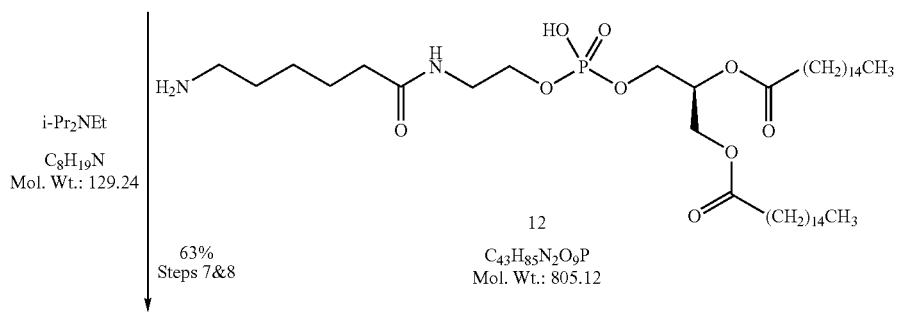

-continued

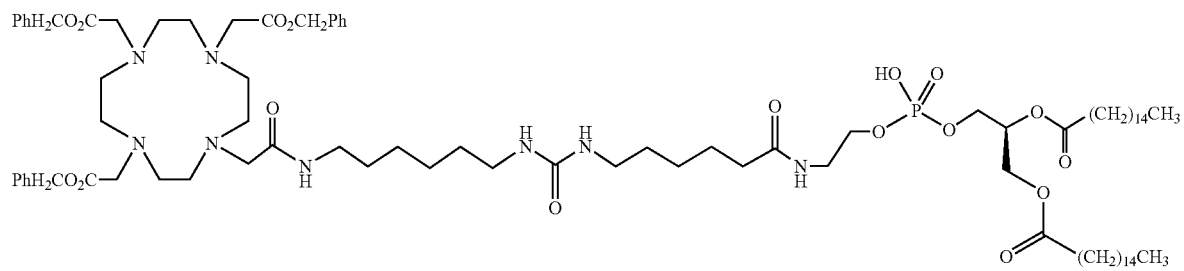

15

C$_{87}$H$_{143}$N$_8$O$_{17}$P
Mol. Wt.: 1604.08

| Materials | Supplier | MW | n [mmol] | Eq. | Amt. |
|---|---|---|---|---|---|
| 8 | | 772.97 | 0.424 | 1 | 0.328 g |
| p-nitrophenyl chloroformate, 13 | Sigma-Aldrich | 201.56 | 0.427 | 1 | 0.086 g |
| i-Pr$_2$NEt | Alfa Aesar | 129.24 | 0.73, 0.73 | 1.7, 1.7 | 100 µL, 100 µL |
| CHCl$_3$ | | | | | 20 mL |
| 12 | | 805.12 | 0.422 | 1 | 0.340 g |

To a 100 mL RB flask was charged 86 mg (0.427 mmol) of p-nitrophenyl chloroformate, 13, and 10 mL CHCl$_3$ (anhydrous). This clear solution was cooled to −10° C. using an ice/salt bath. At −10° C., under argon a solution of 0.328 g (0.424 mmol) of the amine, 8, and 100 µL of i-Pr$_2$NEt in 10 mL CHCl$_3$ was added to 13 over a 25 min period. After an additional 75 min at ca. −5 to −10° C., 340 mg of solid 12 was added. This was followed by a second 100 µL portion of i-Pr$_2$NEt. The reaction mixture turned bright yellow upon the addition of the second portion of i-Pr$_2$NEt. This solution was heated to 50° C. under argon for 20 h. The reaction was allowed to cool to ambient temperature and was then poured into 100 mL H$_2$O and 50 mL CHCl$_3$. The layers were separated and the aq. layer was back extracted with 50 mL CHCl$_3$. The combined CHCl$_3$ layers were extracted with 2×50 mL 0.5 M aq. Na$_2$CO$_3$. After each extraction the aqueous layer was back extracted with 50 mL CHCl$_3$. The combined CHCl$_3$ layers were then extracted with 50 mL H$_2$O and finally with 50 mL brine (again back extracting each aqueous layer with 50 mL CHCl$_3$). The combined CHCl$_3$ layers were dried over MgSO$_4$, filtered and concentrated in vacuo at 35° C. giving a light yellow solid. This solid was slurried in acetone, cooled in refrigerator, filtered through a 0.45 micron syringe filter and the filtrate was concentrated in vacuo at 35° C. giving a pale yellow solid, 15 (430 mg, 63%).

STEP 9

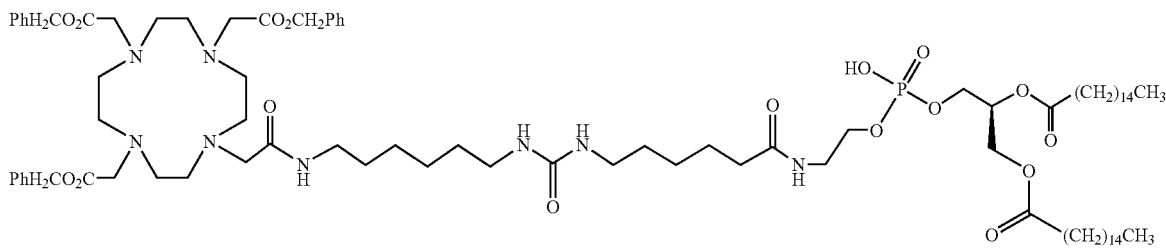

15

C$_{87}$H$_{143}$N$_8$O$_{17}$P
Mol. Wt.: 1604.08

H$_2$, Pd/C
EtOH
85%

-continued

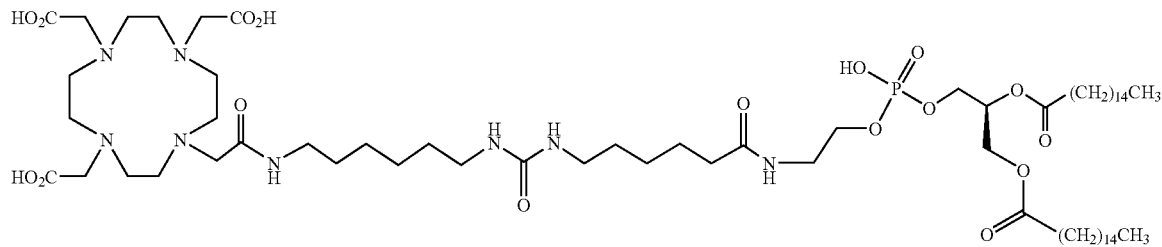

16
C$_{66}$H$_{125}$N$_8$O$_{17}$P
Mol. Wt.: 1333.72

| Materials | Supplier | MW | n [mmol] | Eq. | Amt. |
|---|---|---|---|---|---|
| 15 | | | 0.268 | 1 | 0.43 g |
| Pd/C | Alfa Aesar, 10% Pd | | | | 0.236 g |
| EtOH | | | | | 10 mL |

To a 100 mL 3-Neck RB flask was charged 0.43 g of 15 and 10 mL EtOH. To this clear solution was added 0.236 g of 10% Pd on Carbon. The flask was fitted with a gas inlet line attached to a hydrogen tank, a heavy rubber balloon and a glass stopper. The flask was purged 3× with hydrogen and then enough hydrogen was added to inflate the balloon. The reaction was allowed to stir at ambient temperature for a total of 4 days (periodic addition of hydrogen needed to maintain a positive pressure). The pressure was released and the crude reaction mixture was filtered through a 0.45 micron filter membrane giving a clear filtrate. The solid was washed with 25 mL of 3:1 CHCl$_3$:MeOH. The filtrate was concentrated to a pale yellow solid, 16 (303 mg, 85%).

STEP 10

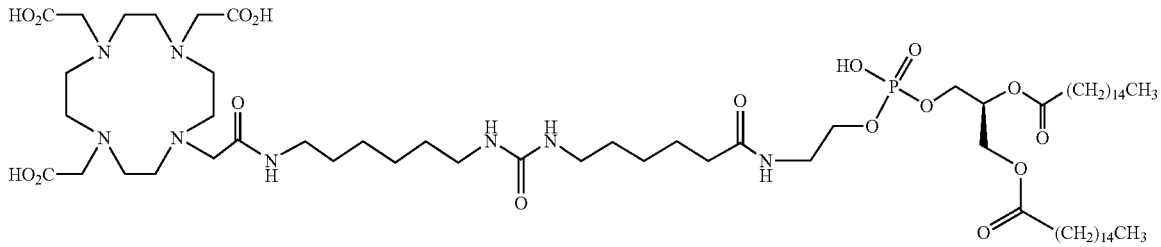

16
C$_{66}$H$_{125}$N$_8$O$_{17}$P
Mol. Wt.: 1333.72 ca. 70% | GdCl$_3$
N-methylmorpholine
CHCl$_3$/MeOH

-continued

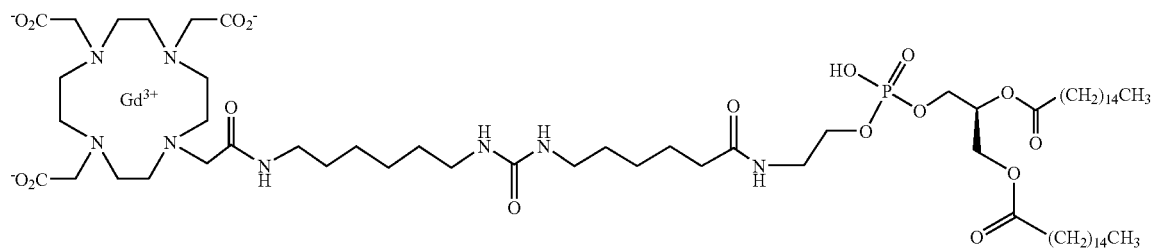

17

$C_{68}H_{122}GdN_8O_{17}P$
Mol. Wt.: 1487.94

| Materials | Supplier | MW | n [mmol] | Eq. | Amt. |
|---|---|---|---|---|---|
| 16 | | 1333.72 | 0.095 | 1 | 0.127 g |
| $GdCl_3$ (anhydrous) | Sigma-Aldrich | 263.6 | 0.106 | 1.1 | 0.028 g |
| N-methylmorpholine | Sigma-Aldrich | 101 | 0.465 | 4.8 | 50 μL |
| $CHCl_3$ | | | | | 2 mL |
| MeOH | | | | | 1 mL |

The gadolinium ion may be introduced into compound 17 following procedures as described in Example 2.

EXAMPLE 5

Targeting

A. DSPE-PEG(2000)-Maleimide Adduct with Targeting Ligand

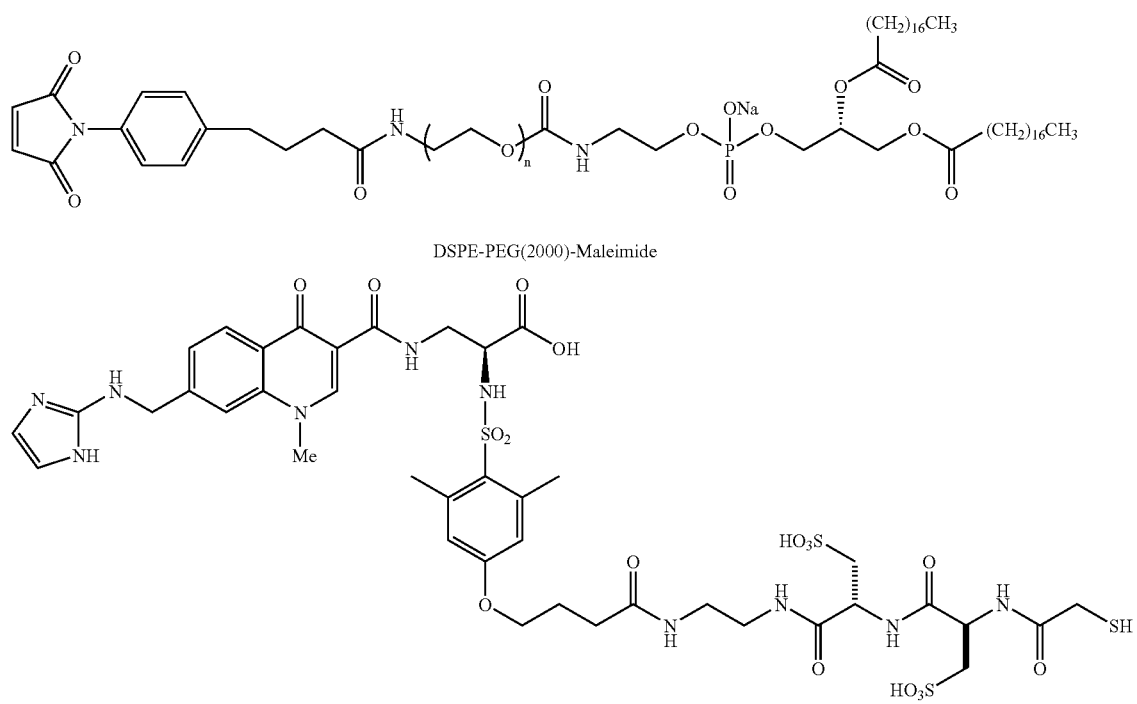

DSPE-PEG(2000)-Maleimide $\alpha_v\beta_3$ Targeting Ligand

DSPE-PEG(2000)-Maleimide is added to αvβ3 targeting ligand with stirring until analysis indicates complete consumption of starting materials giving the composition as shown below wherein the thiol of the αvβ3 targeting ligand has been added to the maleimide of DSPE-PEG(2000)-Maleimide.

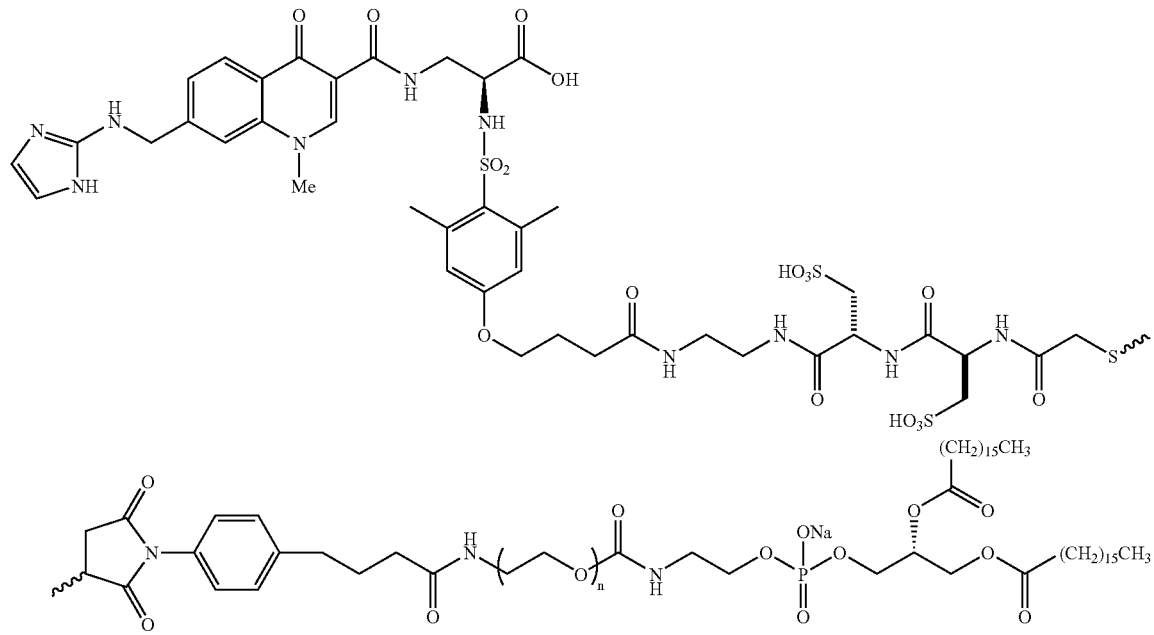

B. Preparation of Nanoparticles:

The paramagnetic nanoparticles are produced as described in Flacke, S., et al., *Circulation* (2001) 104:1280-1285. Briefly, the nanoparticulate emulsions are comprised of 40% (v/v) perfluorooctylbromide (PFOB), 2% (w/v) of a surfactant co-mixture, 1.7% (w/v) glycerin and water representing the balance.

The surfactant of control, i.e., non-targeted, paramagnetic emulsions includes 60 mole % lecithin (Avanti Polar Lipids, Inc., Alabaster, Ala.), 8 mole % cholesterol (Sigma Chemical Co., St. Louis, Mo.), 2 mole % dipalmitoyl-phosphatidylethanolamine (DPPE) (Avanti Polar Lipids, Inc., Alabaster, Ala.) and 30 mole % gadolinium diethylenetriaminepentaacetic acid-bisoleate (Gd-DTPA-BOA, Gateway Chemical Technologies, St. Louis, Mo.).

Tumor-targeted paramagnetic nanoparticles are prepared as above with a surfactant co-mixture that included: 60 mole % lecithin, 0.05 mole % of the conjugate of paragraph B, 8 mole % cholesterol, 30 mole % Example 1 chelate containing $Gd^{3+}$ and 1.95 mole % DPPE.

Tumor-targeted non-paramagnetic nanoparticles are prepared in an identical fashion to the targeted formulation excluding the addition of the lipophilic $Gd^{3+}$ chelate, which is substituted in the surfactant co-mixture with increased lecithin (70 mole %) and cholesterol (28 mole %).

The components for each nanoparticle formulation are emulsified in a Ml 10S Microfluidics emulsifier (Microfluidics, Newton, Mass.) at 20,000 PSI for four minutes. The completed emulsions are placed in crimp-sealed vials and blanketed with nitrogen.

The compounds of the present invention may be used to study tumor models, magnetic resonance imaging and histology procedures, which are known in the art as described below.

C. Tumor Model

Male New Zealand White Rabbits (~2.0 kg) are anesthetized with intramuscular ketamine and xylazine (65 and 13 mg/kg, respectively). The left hind leg of each animal is shaved, sterile prepped and infiltrated locally with Marcaine™ prior to placement of a small incision above the popliteal fossa. A 2 by 2 by 2 $mm^3$ Vx-2 carcinoma tumor fragment, freshly obtained from a donor animal, is implanted at a depth of approximately 0.5 cm. Anatomical planes are re-approximated and secured with a single absorbable suture. Finally, the skin incision is sealed with Dermabond skin glue. Following the tumor implantation procedure, the effects of xylazine are reversed with yohimbine and animals are allowed to recover.

Twelve days after Vx-2 implantation rabbits are anesthetized with 1% to 2% Isoflurane™, intubated, ventilated and positioned within the bore of the MRI scanner for study. Intravenous and intraarterial catheters, placed in opposite ears of each rabbit, are used for systemic injection of nanoparticles and arterial blood sampling as described below. Animals are monitored physiologically throughout the study in accordance with a protocol and procedures approved by the Animal Studies Committee at Washington University Medical School.

At 12 days post-implantation, Vx-2 tumor volumes of animals receiving tumor-targeted (130±39 mm$^3$) or non-targeted nanoparticles (148±36 mm$^3$) were not different (p>0.05).

Twelve New Zealand rabbits implanted with Vx-2 tumors, as described above, are randomized into three treatment regimens and received either:

1) tumor-targeted paramagnetic nanoparticles (tumor-targeted, n=4), 2) non-targeted paramagnetic nanoparticles (i.e., control group, n=4), or 3) tumor-targeted non-paramagnetic nanoparticles followed by tumor-targeted paramagnetic nanoparticles (i.e., competition group, n=4).

In treatment groups 1 and 2, rabbits receive 0.5 ml/kg of tumor-targeted or control paramagnetic nanoparticles following the acquisition of baseline MR images. In treatment group 3, all rabbits receive 0.5 ml/kg tumor-targeted non-paramagnetic nanoparticles two hours before MR imaging followed by 0.5 ml/kg tumor-targeted paramagnetic nanoparticles. Dynamic MR images are obtained at injection and every 30 minutes for each animal over two hours to monitor initial changes in signal enhancement in the tumor and muscle regions. All tumors are resected and frozen for histology to corroborate MR molecular imaging results.

D. Magnetic Resonance Imaging and Histology Procedures

Twelve days after tumor implantation, the animals undergo MRI scanning on a 1.5 Tesla clinical scanner (NT Intera with Master Gradients, Philips Medical Systems, Best, Netherlands). Each animal is placed inside a quadrature head/neck birdcage coil with an 11 cm diameter circular surface coil positioned against the hindlimb near the tumor. The quadrature body coil is used for all radio-frequency transmission; the birdcage coil is used for detection during scout imaging; and the surface coil is used for detection during high-resolution imaging. A 10 ml syringe filled with gadolinium diethylenetriaminepentaacetic acid (Gd-DTPA) doped water is placed within the high-resolution field of view (FOV) and served as a signal intensity standard.

Tumors are initially localized at the site of implantation with a $T_2$-weighted turbo spin-echo scan (TR: 2000 ms, TE: 100 ms, FOV: 150 mm, slice thickness: 3 mm, matrix: 128 by 256, signal averages: 2, turbo factor: 3, scan time: 3 min). A high-resolution, $T_1$-weighted, fat suppressed, three-dimensional, gradient echo scan (TR: 40 ms, TE: 5.6 ms, FOV: 64 mm, slice thickness: 0.5 mm, contiguous slices: 30, in-plane resolution: 250 µm, signal averages: 2, flip angle: 65°, scan time: 15 min) of the tumor is collected at baseline and repeated immediately and 30, 60, 90 and 120 minutes after paramagnetic nanoparticle injection.

Tumor volumes are calculated on an offline image processing workstation (EasyVision v5.1, Philips Medical Systems, Best, Netherlands). Regions-of-interest (ROI) were applied manually around the tumor in each slice of the $T_1$-weighted baseline scan, are combined into a three-dimensional object and the volume calculated.

To quantify image enhancement over time, an unbiased image analysis program is used. $T_1$-weighted images (three contiguous slices through the center of each tumor) collected before, immediately after and 30, 60, 90 and 120 minutes after intravenous nanoparticle injection are analyzed with MATLAB (The MathWorks, Inc., Natick, Mass.). The image intensity at each timepoint is normalized to the baseline image via the reference gadolinium standard. Serial images are spatially co-registered and contrast enhancement is determined for each pixel at each post-injection timepoint. An ROI is manually drawn around a portion of the hindlimb muscle in the baseline images and the average pixel-by-pixel signal enhancement inside the ROI is calculated at each timepoint. A second ROI is manually drawn around the tumor and the standard deviation of the tumor signal is calculated in the baseline image for each animal. Pixels are considered enhanced when signal intensity is increased by greater than three times the standard deviation of the tumor signal at baseline (i.e., enhancement greater than 99% of the variation seen at baseline). Solitary enhancing pixels, those in which all surrounding in-plane pixels do not enhance, are removed from the calculations as noise. The remaining enhancing pixel clusters are mapped back to the immediate, 30, 60 and 90 minute images and the average signal increase at each interval is determined. Statistical comparisons are performed for tumor and muscle for each timepoint using ANOVA (SAS, SAS Institute, Cary, N.C.). Treatment means are separated using the LSD procedure (p<0.05).

After imaging, tumors are resected for histology and immunohistochemistry to verify tumor pathology and assess associated vascularity and angiogenesis. Tumors are frozen (−78° C.) in OCT medium with known orientation relative to original anatomical position and the MRI image planes. Four micron frozen sections (Leica Microsystems, Inc., Bannockburn, Ill.), fixed in acetone at −20° C. for 15 minutes and air dried overnight (4° C.), are stained with hematoxylin-eosin, murine anti-human/rabbit endothelium antibody (QBEND/40, 1:10 dilution, Research Diagnostics, Inc., Flanders, N.J.), or a murine anti-human $\alpha_v\beta_3$-integrin (LM-609, 1:200 dilution, Chemicon International, Temecula, Calif.). Immunohistochemistry is performed using the Vectastain® Elite ABC kit (Vector Laboratories, Burlingame, Calif. 94010), developed with the Vector® VIP kit, counterstained with Vector® methylgreen nuclear counterstain. Slides are reviewed with a Nikon Eclipse E800 research microscope (Nikon USA, Melville, N.Y.) equipped with a Nikon digital camera (Model DXM 1200) and captured with Nikon ACT-1 software.

What is claimed is:

1. A compound of the formula:

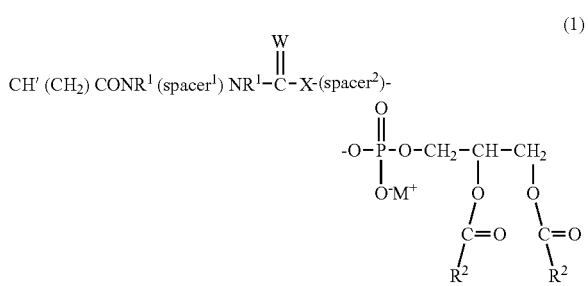

wherein Ch' is a residue of a chelating agent comprising at least four nitrogen atoms and (n−1) carboxyl groups, where n is the number of nitrogen atoms in the chelating moiety;
W is O or S;
X is $NR^1$, S or O;
$M^+$ is a counter-ion;
each $R^1$ is H or alkyl ($C_{1-4}$);
each $R^2COO$ is a residue of a naturally occurring fatty acid or a mixture of said residues;
$spacer^1$ is a $C_{1-10}$ alkyl;
$spacer^2$ is a $C_{1-10}$ alkyl, or

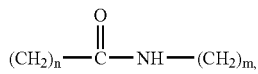

wherein n is 1-6 and m is 1-6;

and wherein said compound is negatively charged when dissolved in water under physiological conditions.

2. The compound of claim 1, wherein $spacer^2$ is $CH_2CH_2$.

3. The compound of claim 1, wherein $spacer^1$ is ethylene, tetramethylene, or hexamethylene.

4. The compound of claim 3, wherein said $spacer^1$ is hexamethylene.

5. The compound of claim 1, wherein Ch' is a residue of 1,4,7,10-tetra-azacyclododecane-N,N',N'',N'''-tetraacetic acid (DOTA) having one less carboxyl group than DOTA.

6. The compound of claim 1, wherein each $R^1$ is H.

7. The compound of claim 1, which further comprising a paramagnetic metal chelated to Ch'.

8. The compound of claim 7, wherein said paramagnetic metal ion is nonradioactive.

9. The compound of claim 1, wherein said compound has the following formula

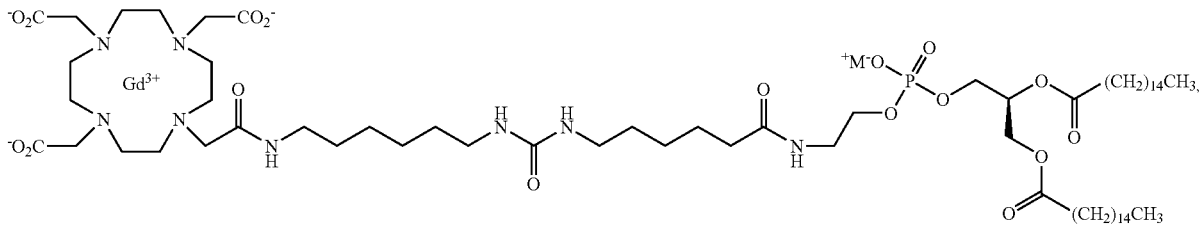

wherein $M^+$ is a counter-ion.

10. The compound of claim 7, wherein the paramagnetic metal ion is Gd(3+).

11. The compound of claim 10, wherein Ch' is a residue of DOTA having one less carboxyl group than DOTA.

* * * * *